(12) United States Patent
Gustafson et al.

(10) Patent No.: US 10,172,662 B2
(45) Date of Patent: Jan. 8, 2019

(54) SURGICAL SCREWDRIVER

(71) Applicants: Peter A Gustafson, Schoolcraft, MI (US); James R Jastifer, Vicksburg, MI (US); Michael J Stoesz, Milwaukee, WI (US)

(72) Inventors: Peter A Gustafson, Schoolcraft, MI (US); James R Jastifer, Vicksburg, MI (US); Michael J Stoesz, Milwaukee, WI (US)

( * ) Notice: Subject to any disclaimer, the term of this patent is extended or adjusted under 35 U.S.C. 154(b) by 582 days.

(21) Appl. No.: 14/733,912

(22) Filed: Jun. 8, 2015

(65) Prior Publication Data

US 2015/0351819 A1 Dec. 10, 2015

Related U.S. Application Data

(60) Provisional application No. 62/008,542, filed on Jun. 6, 2014.

(51) Int. Cl.
| | |
|---|---|
| *A61B 17/88* | (2006.01) |
| *A61B 17/00* | (2006.01) |
| *A61B 90/00* | (2016.01) |

(52) U.S. Cl.
CPC ...... *A61B 17/8875* (2013.01); *A61B 2017/00221* (2013.01); *A61B 2090/066* (2016.02)

(58) Field of Classification Search
CPC .............. A61B 17/8875; A61B 2090/066
See application file for complete search history.

(56) References Cited

U.S. PATENT DOCUMENTS

| | | | |
|---|---|---|---|
| 4,359,906 A | 11/1982 | Cordey | |
| 8,317,791 B2 | 11/2012 | Phan | |
| 2007/0151390 A1 | 7/2007 | Blumenkranz | |
| 2010/0147545 A1* | 6/2010 | Hirt | B25B 23/14 173/182 |
| 2013/0291694 A1* | 11/2013 | Gauthier | B25B 23/1425 81/479 |
| 2014/0165796 A1* | 6/2014 | Gauthier | A61B 17/8875 81/479 |

(Continued)

OTHER PUBLICATIONS

Chapman JR, Harrington RM, Lee KM, et al, Factors affecting the pullout strength of cancellous bone screws. Journal of Biomechanical Engineering. 1996; 118(3):391 398., New York, NY.

(Continued)

*Primary Examiner* — Jan Christopher Merene
(74) *Attorney, Agent, or Firm* — Geoffrey Gelman

(57) ABSTRACT

Various embodiments include a device for driving a fastener into tissue, including a handle having a first and second end. A shank extends from the first end of the handle and terminates in a head. An inertial measurement unit ("IMU") is disposed at the second end of the handle. At least one torque sensor is incorporated in the device. At least one of an indicator or a transmitter is operably coupled to the IMU and the torque sensor. A method of driving a fastener into a tissue with a driver includes recording a previous state and a current state, and using the previous state and current state to predict mechanical properties of the tissue and the optimal torque to be applied. In various embodiment the device predicts a future state of the fastener. The driver notifies the user if the optimal torque has been reached or whether another state has been detected.

7 Claims, 9 Drawing Sheets

(56) References Cited

U.S. PATENT DOCUMENTS

| | | | |
|---|---|---|---|
| 2014/0222012 A1 | 8/2014 | Belkoff | |
| 2015/0025538 A1* | 1/2015 | Kust | B25B 23/14 606/104 |
| 2015/0201918 A1* | 7/2015 | Kumar | A61B 17/1622 606/104 |
| 2015/0282895 A1* | 10/2015 | Theorin | A61B 17/1615 433/165 |

OTHER PUBLICATIONS

Decoster TA, Heetderks DB, Downey DJ, Ferries JS, Jones W., Optimizing bone screw pullout force. Journal of Orthopaedic Trauma. 1990;4(2):169-174., Tampa, FL.

Ricci WM, Tometta P, Petteys T, et al., A comparison of screw insertion torque and pullout strength. Journal of Orthopaedic Trauma. 2010;24(6):374-378., Tampa, FL.

Egol KA, Kubiak EN, Fulkerson E, Kummer FJ, Koval KJ., Biomechanics of locked plates and screws. Journal of Orthopaedic Trauma. 2004;18(8):488-493., Tampa, FL.

Cordey J, Borgeaud M, Perren SM., Force transfer between the plate and the bone: relative importance of the bending stiffness of the screws friction between plate and bone. Injury. 2000;31 Suppl 3 :C21-28. Dorchester, UK.

Thomas RL, Bouazza-Marouf K, Taylor GJ S., Automated surgical screwdriver: automated screw placement. Proceedings of the Institution of Mechanical Engineers, Part H: Journal of Engineering in Medicine. 2008 ;222(5):817-827. Thousand Oaks, CA.

Cleek TM, Reynolds KJ, Hearn TC., Effect of screw torque level on cortical bone pullout strength. Journal of Orthopaedic Trauma. 2007;21(2):1 17 123, Tampa, FL.

Cordey J, Rahn BA, Perren SM. Human Torque Control in the Use of Bone Screws. Current Concepts of Internal Fixation of Fractures. Springer-Verlag: Berlin, Heidelberg, New York; 1980:235 243.

Collinge C, Hartigan B, Lautenschlager EP., Effects of surgical errors on small fragment screw xation. Journal of Orthopaedic Trauma. 2006;20(6):410 4I3. , Tampa, FL.

McGuire RA, St John KR, Agnew SG., Analysis of the torque applied to bone screws by trauma surgeons. Comparisons based on years of experience and material of implant construction. AmJ. Orthop. 1995;24(3):254 256. Parsippany, NJ.

ASTM F543-07: Standard specification and test methods for metallic medical bone screws. 2009, West Conshohocken, PA.

Stoesz, M, Gustafson, P, et al., Surgeon Perception of Cancellous Screw Fixation. Journal of Orthopaedic Trauma, Jan. 2014;28(1):e1-7, Tampa, FL.

Stoesz, M, Gustafson, P, et al., Surgeon Perception of Cancellous Screw Fixation. ASME 2012 Summer Bioengineering Conference, Jun. 2012, Fajardo, PR, USA.

Stoesz, M, Gustafson, P, et al., Surgeon Perception of Cancellous Screw Fixation. Michigan Orthopaedic Society Annual Scientific Meeting. 2012, Jun. 2012, Mackinaw Island MI.

Stoesz, M, Gustafson, P, et al., Surgeon Perception of Cancellous Screw Fixation. 30th Annual Kalamazoo Community Medical and Health Sciences Research Day, 2012, Kalamazoo MI.

\* cited by examiner

500 → ID = 57186896
501 → MaxStiffness = 10093.1 Nmm/deg
502 → MaxTorque = 650.1 Nmm
503 → StiffnessAtMaxTorque = 9311.4 Nmm/deg
504 → FinalAppliedTorque = 650.1 Nmm/deg
505 → time = [...,10.1,10.2,10.3,10.4,10.5,....] s
506 → theta = [...,15.3,18.5,20.2,21.6,22.5,....] deg
507 → pitch = [...,1.2,1.3,0.7,1.0,0.22,....] deg
508 → yaw = [...,4.4,3.2,1.1,2.1,2.5,....] deg
509 → x = [...,7.6,6.9,7.1,6.4,7.4,....] mm
510 → y = [...,67.3,68.0,65.2,67.9,65.3,....] mm
511 → z = [...,121.7,121.4,124.8,122.7,124.8,....] mm
512 → Torque = [...,640.8,642.1,645.3,646.4,646.7,....] Nmm
513 → PredictedFutureTorque = [...,642.6,646.0,646.5,645.8,648.7,....] Nmm
514 → ErrorFromPredictedTorque = [..., -0.6,-0.5,-0.7,-0.1,0.9,....] Nmm
515 → PredictedMaxTorque = [...,702.1,705.6,705.6,705.6,....] Nmm
516 → Force = [...,113.8,112.0,108.3,107.5,119.0,....] N
517 → Additional Fields ...
518 → CommunicationState = [...,continue,continue,warning,warning,stop,....]

Figure 5

SURGICAL SCREWDRIVER

RELATED APPLICATIONS

The present application claims the benefit of priority of U.S. provisional patent application No. 62/008,542, entitled "SURGICAL SCREWDRIVER", and filed Jun. 6, 2014, the entirety of which is hereby incorporated by reference herein for all purposes.

FIELD

The present disclosure is in the field of a driver to insert fasteners in tissue, including without limitation, the insertion of screws and other fasteners into bone.

BACKGROUND

Orthopedic surgeons use screws and similar fasteners in combination with plates and other medical devices for internal fixation and stabilization. Fasteners are useful in the treatment of fractures and in other circumstances such as arthroplasty. Surgeons are generally guided by experience and intuition in performing surgical procedures where screws are tightened, and stop based on "feel." However, human tissue has variability of mechanical properties, due to age, anatomic location, bone density, nutrition, load history, and numerous other reasons. Stripping of the bone or screw or fastener malposition can lead to unstable fixation and a reduction in treatment effectiveness. Consequences include increased reoperation rates, morbidity, and mortality. Studies using synthetic bone indicate that surgeons may strip the tissue (cause yield, fracture, or failure due to over-torquing) up to 40% of the time when driving screws into tissue at torque levels relevant for fixing osteoporotic bone.

SUMMARY

Various embodiments include a device for driving a fastener into tissue, including a handle having a first and second end. A shank extends from the first end of the handle and terminates in a head. A continuous position sensor is operably coupled to the device. At least one torque sensor is incorporated in the device. At least one of an indicator or a transmitter to transmit a signal to a secondary device having an indicator, is operably coupled to the position sensor and the torque sensor. Optionally, the shank may be attached to a ratchet, facilitating the mechanical application of twist.

Various embodiments include a method of driving a fastener into a tissue with a driver, including the steps of recording a previous state of the driver at $t_0$, including a first torque measurement and a first position measurement. The current state of the driver at $t_1$ is detected, including a second torque measurement and a second position measurement. In various embodiments, the driver may be cycled multiple times through the same position, in order to obtain additional measurements and/or states of the driver at the given position. In some embodiments, as the driver is cycled through the same position, the fastener is cycled through the same position as well (e.g., alternately advancing and receding). Mechanical properties of the patient's tissue are predicted based on the previous state and the current state. A desirable torque measurement is predicted based on the previous state and the current state or based on the plurality of states. It is determined whether the predicted desirable torque measurement has been reached based on the second torque measurement or based on the plurality of states.

Various embodiments include a method of advancing a fastener into a tissue with a driver, comprising the steps of recording a previous state of the driver at $t_0$, including a first torque measurement and a first position measurement. A predicted future state of the driver at $t_1$ is predicted, including a second torque prediction and a second position prediction based on a desirable anatomic location for the fastener and the previous state. A current state of the driver at $t_1$ is detected including a second torque measurement and a second position measurement. The predicted future state is compared to the current state to determine whether the fastener is advancing as predicted to notify a user if the fastener is not advancing as predicted.

BRIEF DESCRIPTION OF THE DRAWINGS

FIG. 5 is a depiction of a data structure for storing information related to a procedure, according to some embodiments.

DETAILED DESCRIPTION

Figure 1:
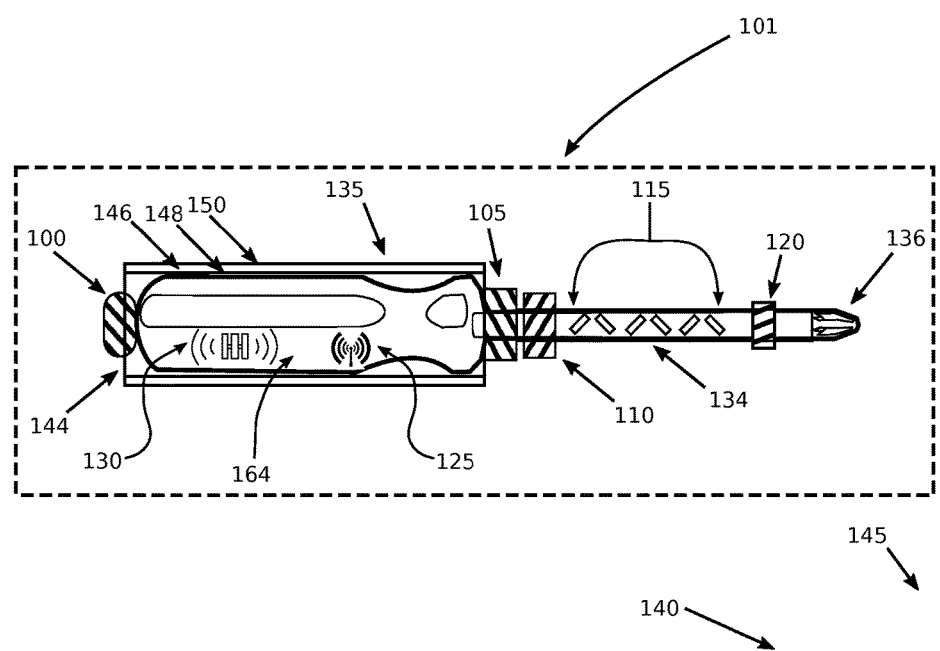
FIG. 1 is a side elevation view of a driver according to various embodiments.

For purposes of description herein the terms "upper," "lower," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings, and described in the following specification are simply exemplary embodiments. Hence, specific dimensions and other physical characteristics relating to the embodiments disclosed herein are not to be considered as limiting, unless the claims expressly state otherwise.

Fasteners such as those described herein may be used in various procedures, in addition to fixation of bones using plates and screws as further described below. The use of a device for inserting a fastener into a bone represents just some of the contemplated embodiments. Therefore, as used herein, the term "screw," includes all such fasteners that are driven into bone or other tissue by twisting the fastener, the "tissues" described herein include various tissues of the body, whether boney, cartilaginous, or other tissues.

An assembly including plates and fasteners such as screws is often used by surgeons to achieve osteosynthesis through fixation of bones in the desired relative orientation with the fixation assembly. The goal of such fixation is to achieve a stable environment that promotes bone healing. Screw pullout strength is a factor that contributes to the stability of the fixation assembly, as is the capacity of the fixation assembly to resist motion between the plate and the bone. Sufficient friction to reduce or eliminate motion between the plate and the bone is generated by achieving adequate compressive force at an interface between the plate and the bone, and the compressive force is related to the torque applied to the screw.

Achieving stable fixation can be difficult in osteoporotic, comminuted, or cancellous bone, as screws are more susceptible to pullout and shear failure in these circumstances, and are therefore less able to generate compressive force between the plate and the bone. The amount of screw torque required to resist motion under certain physiologic loading conditions is preferably at least 3 Nm. This amount is relative, given various clinical settings, though the importance of optimizing screw torque becomes most clinically relevant in low density bone. In these situations, the surgeon's goal may be to achieve a torque that maximizes the load carrying capacity of the fixation assembly without compromising the structural stability of the bone through stripping of the screw or bone.

Figure 7:
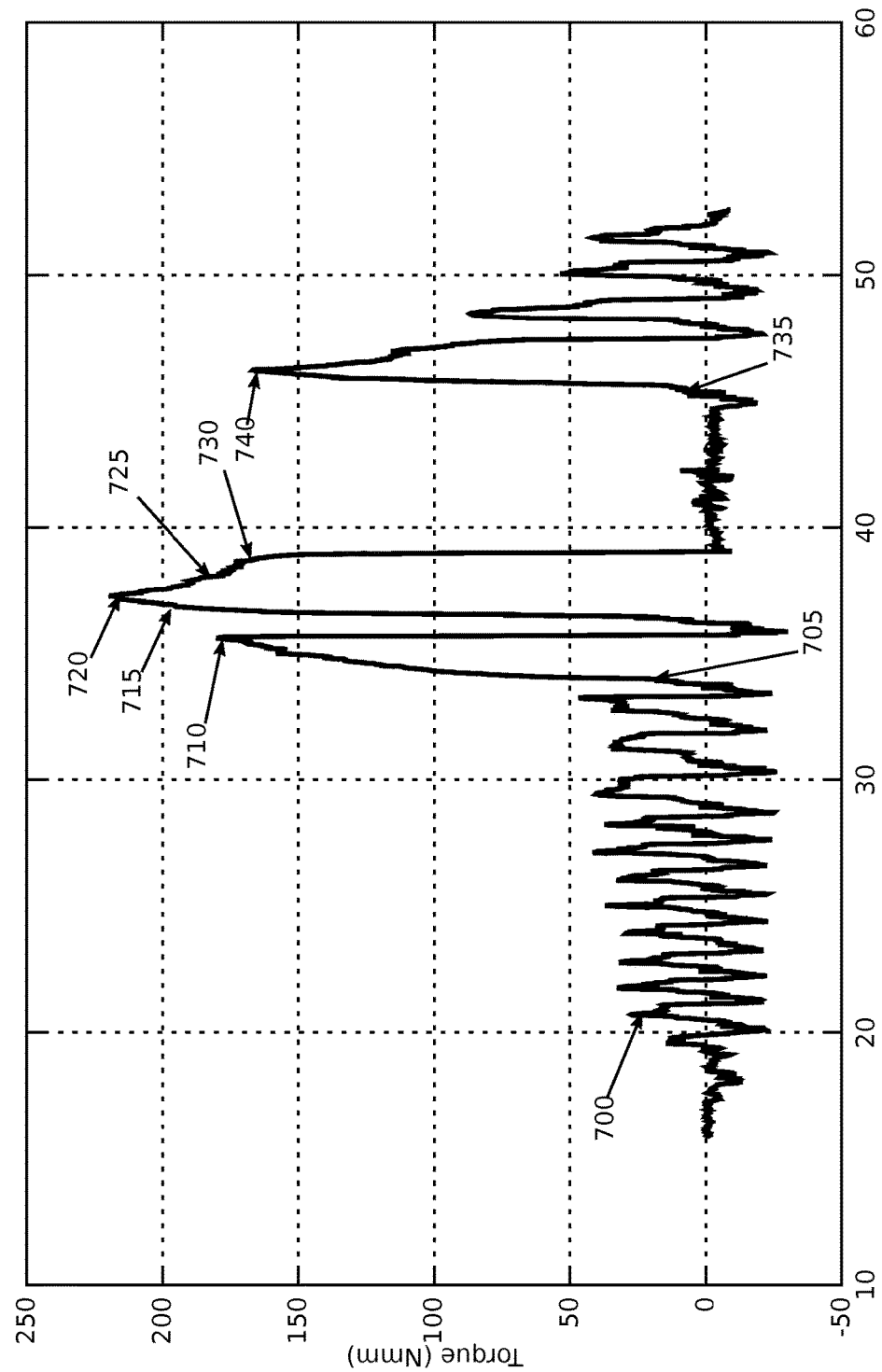
FIG. 7 is a graphical representation of a measured torque with respect to time during insertion of a screw into tissue, according to various embodiments.

FIG. 7 schematically shows a measured torque curve during the insertion of a screw into tissue. Time is denoted on the x-axis, which corresponds with the amount of twist the surgeon has applied to the screw. Torque is denoted on the y-axis. In the example depicted in FIG. 7, the surgeon continued to drive the screw past the point where the screw stripped the bone (e.g., as denoted by point 720), as indicated by the subsequent reduction in measured torque $T_I$ (i.e., at point 740). In the example depicted in FIG. 7, the surgeon bypassed maximum torque $T_M$ (at point 720).

Figure 6:
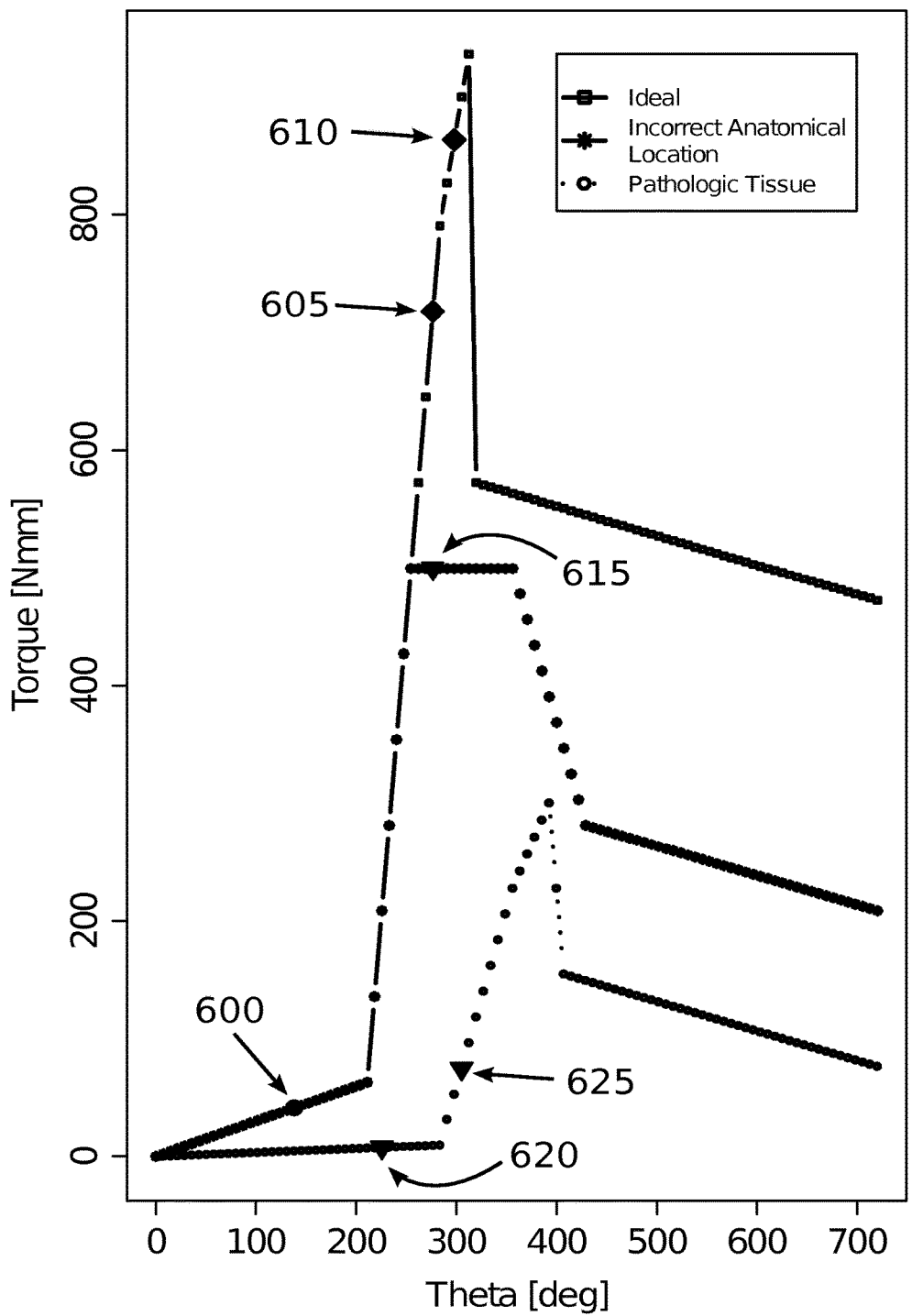
FIG. 6 is a graphical representation of torque with respect to screw rotation, according to various embodiments.

As shown in FIG. 6, in the plot for the "ideal case", the torque rises linearly during the first phase of screw insertion (a phase which includes point 600) as an increasing number of threads of the screw come into contact with the bone. Once the screw head contacts the plate, further advancement causes tightening, during a tightening phase (a phase which includes point 605). During the tightening phase, torque rapidly increases at an approximately constant rate related to the material modulus of the bone, until the bone reaches a yielding point. The yielding point likely occurs between 70% to 90% of a maximum torque point and screw advancement past this yielding point decreases pullout strength. If screw advancement does continue past the yielding point, torque continues to increase (during a phase containing point 610) until a maximum torque $T_M$ is reached. If screw insertion continues beyond the maximum torque point, bone stripping occurs during a stripping phase, and torque rapidly drops. Stripping of the bone during the stripping phase dramatically decreases screw pullout strength by as much as 82% and ultimately affects the stability of the fixation assembly. Eventually, the torque will reach a plateau, as the bone is permanently deformed.

As will be appreciated, the plots in FIG. 6 are representative plots for one or more representative tissue samples. However, due to variations in tissue (e.g., due to natural variations), in an actual procedure, one or more phases visible in FIG. 6 may not be present or observable.

In typical insertion of screws by surgeons, surgeons subjectively determine the amount of torque that will be tolerated based on perception of bone quality and attempt to discontinue insertion prior to stripping. In many cases, particularly when the screw will be inserted into osteoporotic, metaphyseal, or other compromised bones, the surgeon will attempt to maximize plate compression by approaching maximum screw torque. However, as described above, bone yielding may occur at the screw-bone interface prior to achieving maximum torque. Furthermore, if maximum torque is exceeded, and stripping occurs, the surgeon may not recognize this condition. Surgeon perception of screw stripping varies considerably from surgeon to surgeon.

Additionally, certain clinical scenarios require the surgeon to make determinations regarding the anatomic location of the screw within the tissue. For example, during insertion of the screw into a spinal pedicle, the surgeon must determine whether the screw is advancing within the boney portion of the spinal pedicle rather than the surrounding tissue. To make this determination, the surgeon evaluates the actual torque that is required to tighten the screw as compared to the amount of torque that the surgeon expected to be required. For example, if the screw is easier to turn, requiring less torque than expected by the surgeon, then the surgeon may determine that the screw has been inserted into tissue that is not the spinal pedicle. Perception of correct screw location within the tissue can also vary considerably between surgeons.

A driving device 101 (also called a "driver" herein) is shown in FIG. 1. The driver may be intended to aid surgeons in reaching a desired torque and/or a torque from within a desired range of torques for inserting a fastener into a tissue. To that end, the driver may include sensors (as further described below) to measure torque, twist, displacement, and other variables as described in detail herein, and provides feedback to the surgeon as the fastener is inserted to notify the surgeon of the impending arrival of the desired torque and when the desired torque has been reached or exceeded. A driver 101 according to the various embodiments could be used in surgical procedures to prevent over-twisting of screws during surgery, to assist in correct anatomic placement of screws or to train surgeons to effectively tighten fasteners without tightening or twisting too much.

The driving device 101, according to various embodiments may include a handle 135, a shank 134 extending from the handle 135, and a head 136 at the end of the shank 134 opposite the handle 135. Optionally, the shank and handle may be joined at a ratchet 105. The driving device may include a torque sensor and/or torque cell 110.

The order of the ratchet and torque cell may be swapped in various embodiments. In various embodiments, the order is head, shank, torque cell, ratchet, handle. In such embodiments, there would be a direct measure of torque passed to the head, thus avoiding frictional losses in the ratchet. Where other priorities for measurement fidelity exist or for other reasons, alternate embodiments may be employed.

The driving device 101 may be used by surgeons to insert fasteners, with the surgeon applying torque to twist the handle 135 of the driver 101 and transferring the motion to the fastener through mechanical engagement of the head 136 with corresponding features in the fastener. Such features may include a "cruciform" or "hex" or "square" or "star" or "slot" or similar indentation in which the complementary head of the driver may fit.

In the embodiments depicted in FIG. 1, a continuous position measurement device, here an inertial measurement unit 100 (also referred to as an "IMU" herein), is disposed at an end 44 of the handle 135 opposite the shank 134. In a various embodiments, the IMU may be capable of sensing three translational and three rotational degrees of freedom. In various embodiments, the IMU includes a magnetometer with three degrees of freedom. The IMU may thus have nine or more sensing degrees of freedom. In various embodiments, it will be appreciated that "position" includes all translational, rotational, and magnetic degrees of freedom or any subset of these degrees or freedom. The IMU may include, for example, a unit manufactured by Sparkfun, or by any other manufacturer. The IMU 100 may measure the position, velocity and acceleration of the driver 101 in translational and rotational degrees of freedom. In various embodiments, the IMU 100 can isolate backward twist, forward twist, and advancement or removal of the driver 101. The IMU 100 allows the driving device 101 to provide a count of the number of degrees the fastener has been rotated since initiation of contact with the head 136 and measures how far the fastener has advanced. The collection of velocity and acceleration data by the IMU 100 also allows for information to be provided to the surgeon regarding the rate, such as when to slow the rate at which the fastener is driven.

In various embodiments, the driver includes a transmitter 125. In various embodiments, the transmitter 125 may be a transceiver, capable of both transmitting and receiving. In various embodiments, the transmitter may be situated inside the handle 135. The transmitter may be a wireless transmitter. The transmitter may transmit using any suitable technology or protocol. The transmitter may transmit using Blue-tooth, Wi-Fi, cellular, infrared, Near Field Communication, and/or using any other means of communication. The transmitter may be used to transmit signals from the driver 101 to a separate device, such as to a computer 140.

Signals transmitted from the driver 101 to a separate device may include signals indicative of measurements, sensor readings, times at which measurements were taken, inferences about the current state of the procedure, predictions about the future state of the procedure, directions for an operator, alerts for an operator, information for an operator, and/or any other information.

In various embodiments, the transmitter 125 may be a transceiver capable of both transmission and reception. In such an embodiment, all signals described as being transmitted from the driver 101 to a separate device 140 may also be transmitted from the separate device 140 to the driver 101. The separate device may therefore be used for any computational task otherwise described as being processed by the driver. An exemplary embodiment may have the driver 101 transmit measured sensor data to the separate computing device 140 where that device may compute derivatives of the sensor data and execute processes based on the relationships of those derivatives and the measured sensor data. The separate device may then transmit signals and instructions to the driver and the driver may respond as if the processes were computed on the driver.

In various embodiments, the driver may communicate with an external device via a wired connection, such as via Ethernet cable, universal serial bus (USB) cable, fiber optic, or via any other means of communication.

In various embodiments, at least one torque sensor is provided in the driver 101. In the embodiments depicted in FIG. 1, there are a plurality of redundant torque sensors. Any single torque sensor depicted in the embodiments shown in FIG. 1, or combination thereof, could be used in a given embodiment. A first torque sensor 146 is included in the handle 135. The handle 135 incorporates a first cylinder 148 and a second cylinder 150 concentrically arranged. Differential rotation of the first cylinder 148 and the second cylinder 150 indicates torque applied to the handle 135 by the surgeon. The transmitter 125 may transmit the differential rotation of the concentrically arranged first cylinder 148 and second cylinder 150. Also, as shown in the embodiments depicted in FIG. 1, reaction torque load cell 110 is positioned at the juncture of the shank 134 and the handle 135. There is also a ratchet between the handle and shank. A plurality of strain gauges 115 oriented for shear strain and torque measurement are positioned in the shank 134. Additional strain gauges or load cells, not depicted, can optionally be used to measure axial forces, bending forces, moments, or distortion on the driver 101.

Indicators are also provided on the driver 101, to provide feedback to the surgeon. As shown in FIG. 1, one of the various indicators includes an LED indicator 120 located on the shank 134, near the head 136, in a location that is viewable to the surgeon while operating the driver 101. Additionally, motion generators 130 can be provided in the handle 135 of the driver 101, to provide haptic feedback to the surgeon through vibration of the handle 135. A speaker 164 may also be provided in the driver 101, to provide an audible signal to the surgeon. The indicators for use with the driver 101 can be used to transmit information to the surgeon to warn of approaching the optimal torque, to warn when the optimal torque has been reached, or to warn when the optimal torque has been exceeded.

As used herein, the terms "optimal torque" and "desired torque" may refer to a torque or range of torques above which the risks of further advancement of the fastener may outweigh the potential benefits of further advancement. In other words, the risks of causing undesired bone damage may outweigh the potential benefits to be had from any potential or realized increase in hold strength. The optimal torque need not be fixed or precise value in all cases. In various embodiments the optimal torque may depend in part on a subjective judgment of risks and benefits, on the needs of a particular patient, etc. In various embodiments, an "optimal torque" is simply a threshold torque, such that it is deemed desirable, advisable, or otherwise prudent to stop the further advancement of the driver any further once the optimal torque has been reached. As will be appreciated, the "optimal torque" need not be a torque that is objectively the best assuming perfect knowledge of all relevant variables. Rather, in various embodiments, the "optimal torque" may represent a current determination, calculation, or other estimate as to a value of torque above which further advancement of the driver should stop.

In various embodiments, transmitter 125 may be used to transmit measurements from the IMU 100 and any torque or force sensors 146, 105, 115 to a separate processor, such as a computer/computing device 140. Indicators, such as visual or aural indicators can also be incorporated into the computing device 140 to provide information to the surgeon about reaching the optimal torque (such as lights displayed on a computer monitor, other visual signals displayed on the computer monitor, a sound transmitted through computer speakers, etc.). Additionally, the computing device 140 may include a display to show a graph incorporating the measurements of torque, position, rotation, time, and their derivatives, allowing the surgeon to visualize the torque curve or other measures of state. By visualizing the torque curve or other measures of state, the surgeon is better able to anticipate the optimal torque of the fastener and avoid over-tightening beyond the optimal torque.

In certain embodiments, the driver 101 may include a sealed handle 135 and sensors 146, 105, 115, with an inductive charging unit to allow sterilization. In other embodiments, the driving device 101 can be manufactured for one-time use and disposed of following the first use.

In use, according to various embodiments, the driver 101 is positioned as desired by the surgeon. The surgeon then applies a torque to twist the driver 101. Mechanical engagement of the head 136 of the driver 101 with the fastener transfers the forces applied to the driver 101 to the fastener, which is then driven into the desired tissue.

Figure 3:
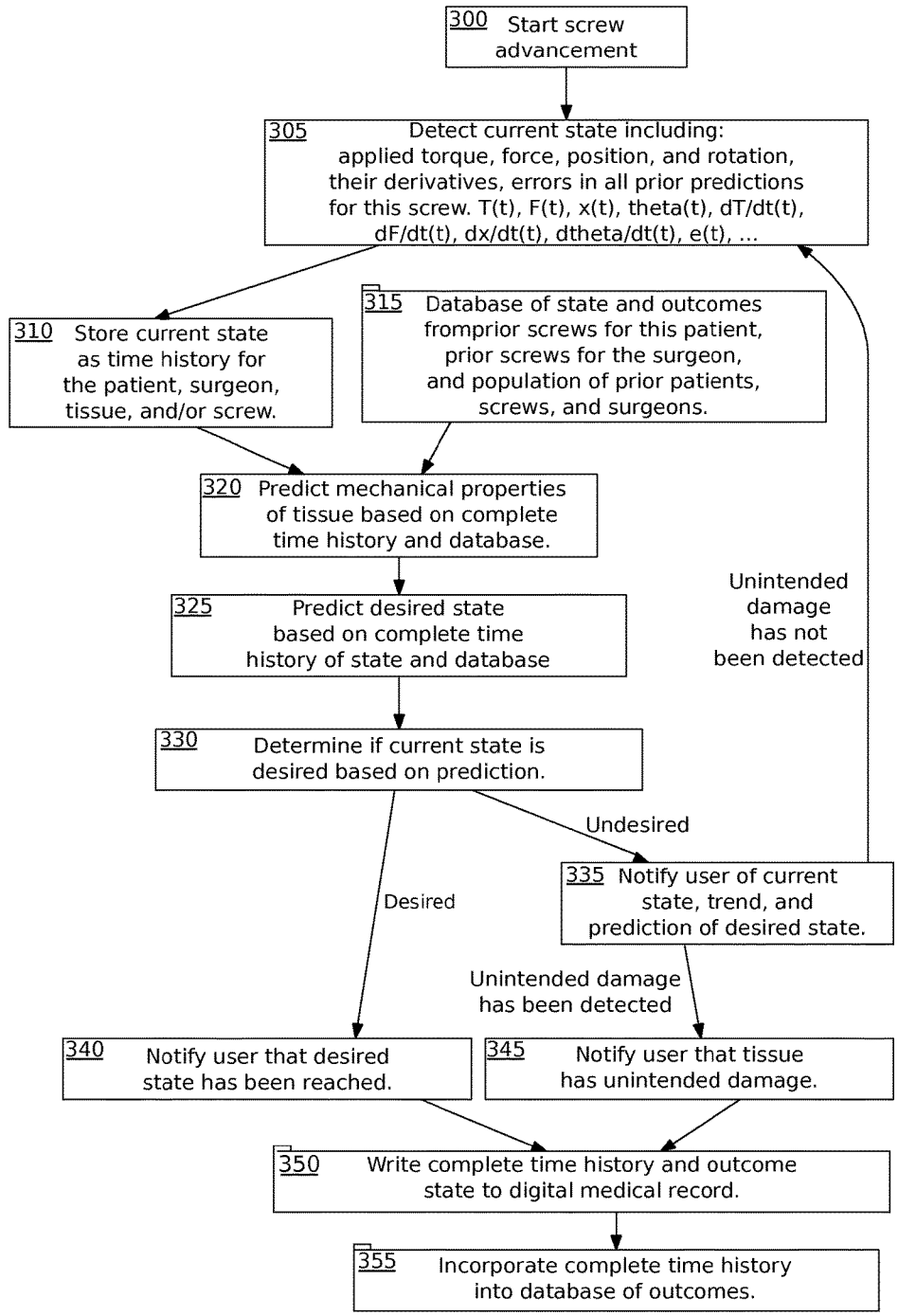
FIG. 3 is a flow chart illustrating a method for inserting a screw according to various embodiments.

The measurements collected by the sensors 146, 105, 115 on the driver 101 as depicted in FIG. 1, allow the driver 101 to carry out the algorithms and processes depicted in FIG. 3.

Figure 2:
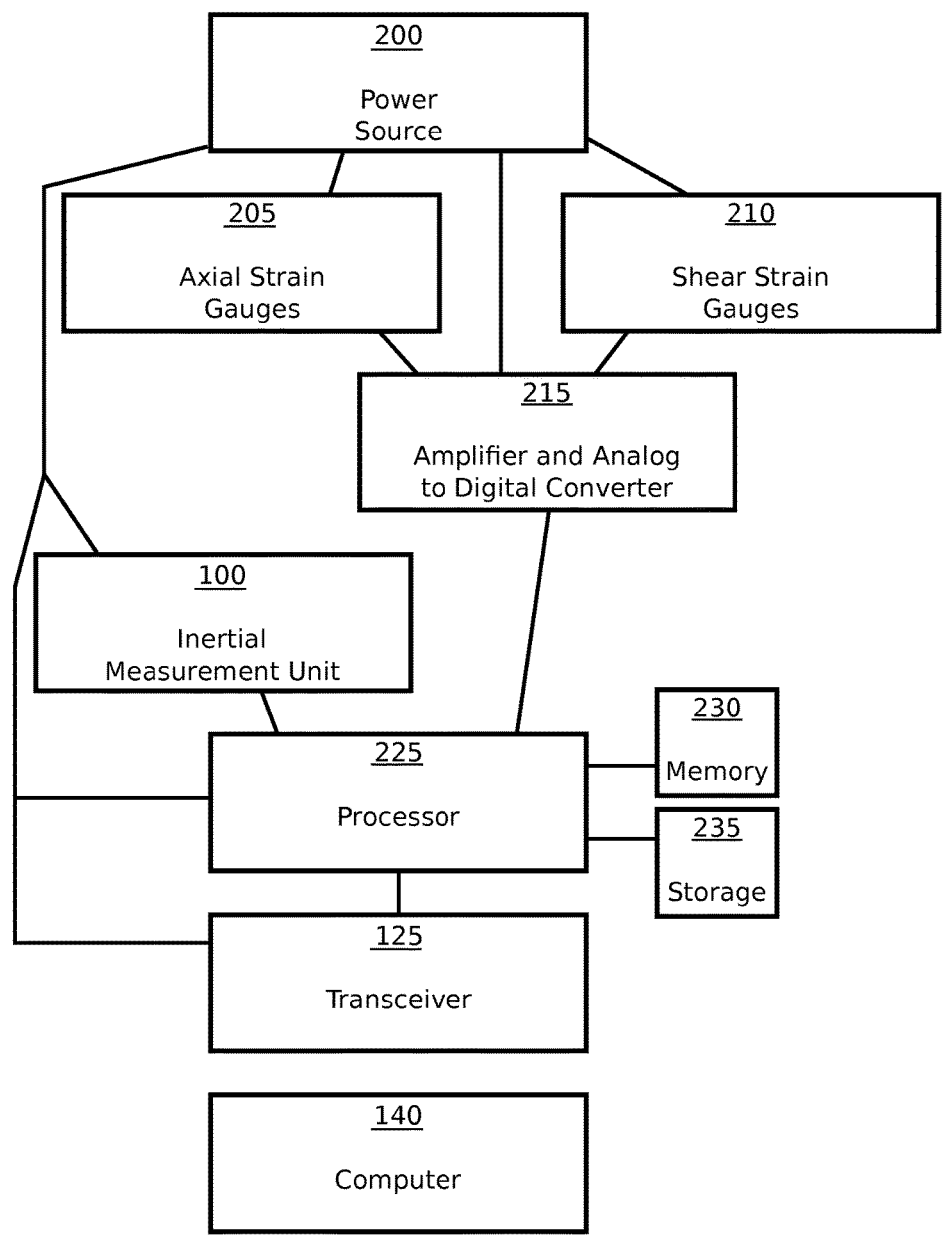
FIG. 2 is a logical diagram of a system according to various embodiments.

With reference to FIG. 2, a logical block diagram is shown illustrating a system according to some embodiments. The system may include a driver and a separate computer/computing device. A power source 200 within the driver 101 may provide power to other electronic or mechanical components within the driver. The power source may include a battery, a super-capacitor, a fuel cell, a converter or adapter for grid power (e.g., in the event that the driver is plugged into a wall outlet), a converter or adapter for another source of power (e.g., a separate battery pack, e.g., power over Ethernet, e.g., power over USB), or any other power source.

Processor 225 may include a standard central processing unit, such as an Intel Core i7, an Intel Atom processor, a Qualcomm Snapdragon, or any other processor. Processor 225 may include a digital signal processor, field programmable gate array, application-specific integrated circuit, logic circuit, or any other logic. The processor may be in communication with one or more sensors, including one or more axial strain gauges 205, one or more shear strain gauges 210, and/or one or more inertial measurement units 100.

In various embodiments, an Analog to Digital Converter 215 may serve as an intermediary between one or more sensors and the processor 225. The converter 215 may convert analog readings from the sensor into digital form for use by the processor. The converter 215 may also include an amplifier.

The processor 225 may be in communication with a transceiver 125. The transceiver may be capable of communication with a remote device. Communication may be wireless or wired, as described above. In various embodiments, communication may be one way (e.g., from the driver to an external computer). In various embodiments, communication may be two-way.

The driver may include a data storage device 235. The data storage device may include a hard disk, solid state drive, flash memory, magnetic memory, holographic memory, and/or any other storage means.

The driver may include memory 230. Memory may include dynamic random access memory, or any other suitable type of memory.

The processor may be in communication with the data storage device 235 and with memory 230.

In various embodiments, the driver may store (e.g., in data storage 235; e.g., in memory 230) one or more programs for use in carrying out steps in accordance with one or more embodiments. The processor 225 may execute such programs for carrying out such steps.

An external computing device 140 may be in communication with the driver (e.g., by wired or wireless communication). The computing device may receive measurements, warnings, directions, data, etc. from the driver. Received communications may be displayed for an operator, stored for future reference (e.g., in a current procedure; e.g., in a future procedure) used to derive inferences about the current procedure, and/or for any other purpose.

In various embodiments, the computing device may include its own processor, memory, data storage, input devices (e.g., mouse, keyboard), output devices (e.g., speaker, display), and/or any other components.

The computing device may store (e.g., in data storage; e.g., in memory) one or more programs for use in carrying out steps in accordance with one or more embodiments. The processor of the computing device may execute such programs for carrying out such steps.

It will be appreciated that the components and arrangements of components depicted in FIG. 2 represent just some embodiments, and are not intended to be limiting. Various embodiments contemplate the use of additional components, substitute components, and/or fewer components. In various embodiments, certain components may be combined (e.g., a processor may include integrated memory). In various embodiments, certain components may be separated. For example, in various embodiments, steps or computations performed may be distributed among two or more separate processors and/or may be performed in the cloud. Data stored may be separated across two or more physical device and/or may be stored in the cloud. In various embodiments components may be connected to one another in different ways than the ways depicted in FIG. 2. There may be more connections in some embodiments. There may be fewer connections in some embodiments.

In various embodiments, all functions may be performed by a single device (e.g., by the driver). In some embodiments, there may be more than one off-board or separate computing device.

With reference to FIG. 3, a flow diagram is depicted illustrating steps that may be carried out by the driver and/or separate computing device in accordance with one or more embodiments.

As will be appreciated, the steps illustrated in FIG. 3 represent steps that may be carried out according to some embodiments, but such steps are not intended to be limiting. Various embodiments contemplate the use of more steps, fewer steps, and/or steps that are carried out in a different sequence. Additionally, various steps that are depicted as a single step in FIG. 3 may be carried out as multiple steps, including as multiple steps with other intervening steps. Further, multiple steps that are depicted in FIG. 3 may, in various embodiments, be carried out as a single step. According to various embodiments, steps depicted in FIG. 3, or otherwise contemplated in various embodiments, need not be carried out in a strictly linear or serial fashion, but may be carried in parallel, in overlapping fashion, in a distributed fashion, or in any other fashion. Further, various embodiments contemplate that certain steps depicted in FIG. 3 are carried out only partially. For example, in various embodiments, only a subset of the measurements listed at step 305 are taken.

According to various embodiments depicted in FIG. 3, a surgeon uses the driver 101 to insert a screw into bone tissue. The surgeon begins at step 300 by advancing the screw with the driver 101, first by aligning the head 136 of the driver with the corresponding features of the screw (e.g., with an indentation in the head of the screw). The driver 101 is then rotated to begin screw advancement. As the driver 101 is advanced, at step 305 it measures a current state of the procedure, driver 101, and/or screw at a time (t), including factors such as the torque applied to the screw (T(t)), the force applied to the screw (F(t)), the position of the driver 101 (x(t)), and the rotation of the driver 101 ($\theta$(t)). The driver 101 also calculates the derivatives of these measurements (e.g., dT/dt(t), dF/dt(t), dx/dt(t), d$\theta$/dt(t)) and the errors in some or all prior predictions (e(t)) for the screw being advanced.

Derivatives can be calculated and/or tracked in various ways, according to various embodiments. In various embodiments, derivatives, and any other derived values, may be tracked in analog via one or more circuit elements and/or via one or more circuits. For example, if a sensor outputs a voltage reading that is proportional to θ(t), then a current reading across a capacitor connected to the sensor may be proportional to dθ/dt(t), since the current across a capacitor is proportional to the time derivative of the voltage across the capacitor. It will be appreciated that various other circuit elements or circuits may likewise be used, and that other types of measurements may likewise be tracked, in various embodiments. In various embodiments, analog values may be sampled (e.g., periodically sampled), discretized, and/or otherwise converted into digital form.

Note that, the measured variables may represent vectors and may therefore include multiple components (e.g., one component for each dimension). Thus, for example, a measurement of a position may include a measurement of an x, y, and z position and/or rotations about x, y, and z.

In various embodiments, the driver, or separate computing device, may attempt to predict one or more measurements. If there is a prediction of what a given measurement was expected to be, the predicted value may be compared to the actual value, and an error may be determined. The error may be stored. In various embodiments, the size of the error may serve as an indication of the state of the procedure. E.g., a large error may indicate that the procedure is not proceeding normally.

In one method of predicting desired torque, the driver may be stopped, reversed, or cycled while the above measurements are obtained. Stopping, reversing, or cycling may done mechanically by the surgeon or, in some embodiments, may be facilitated by the ratchet or by means of an automated driver. This stopping, reversing, or cycling provides additional states. The relation of these states to each other and over time are indicative of current and likely future state. The states also offer a direct indicator of damage or stripping if it has occurred.

At step 310, the measurements for the current state at time t are also in the memory of the driver 101, and can be maintained in a history of the driver 101 further identified by the patient, bone, screw, and/or surgeon to which the measurements relate. Therefore, one or more databases associated with the driver 101 are maintained with the current state at time t (and at a plurality of previous states at times t', t", t''', etc.) and outcomes relating to prior screws inserted into the particular patient, into the relevant bone of the particular patient, by the relevant surgeon, and/or overall with respect to populations of prior patients, prior inserted screws, and all surgeons.

At step 315, the driver may access a database that may include historical information that may be useful for making inferences and/or predictions regarding the current procedure. Historical information may include information from prior procedures, prior procedures with the current patient, prior procedures with other patients, prior procedures with the current type of screw, prior procedures with other types of screws, and/or information about any other procedure.

At step 320, information regarding the state of the driver 101 at time t and the databases associated with the driver 101 of current state measurements, previous state measurements, and outcomes are used to predict mechanical properties of the bone. These predictions can be based on the complete or partial history of the particular screw, from the time the driver 101 begins to advance the screw, or even before the screw reaches the bone tissue.

At step 325, the predicted mechanical properties of the bone are used to additionally predict the desirable state of the screw, e.g., the amount of torque to be applied at time t (T(t)). After predicting the optimal state, the driver 101 compares the current state to the optimal state, to determine if the optimal state has been reached.

At step 330, if a desirable state has been reached, flow proceeds to step 340, where the driver 101 notifies the user that the desirable state has been reached, using at least one of the various indicators 120, 130, 164, and computing device display, described above. If the desirable state has not been reached, then flow proceeds to step 335, where the driver 101 optionally notifies the user of the current state, the trend (e.g., whether advancement is continuing as predicted), and a prediction of when the desirable state will be reached. If the driver 101 detects that the desirable state has not been reached, and also has not detected measurements which indicate that an unsatisfactory state has occurred, then flow cycles back to step 305, where the driver 101 will continue to detect the current state of the driver 101 as the surgeon continues to advance the screw. Where the driver 101 has detected characteristics that indicate that the bone has been undesirably damaged (e.g., if there is a sudden decrease in torque as the screw is advanced) or another unsatisfactory state has been reached, such as suspected anatomical misplacement of the screw, then flow proceeds to step 345, where the driver 101 notifies the user of the unsatisfactory outcome.

Also as shown in FIG. 3, once the desirable state has been reached or an unsatisfactory outcome has been detected, or when the surgeon otherwise stops advancing the screw, flow proceeds to step 350, where the driver 101 can also be used to transmit a set of data associated with the screw as measured by the driver 101 to a medical record of the patient. The set of data can include information relating to the type of screw, the surgeon, the current state measurements collected, whether the desirable state was reached, and any other relevant measurements. In certain embodiments, the same set of data is also incorporated into the databases associated with the driver 101. In other embodiments, flow proceeds to step 355, where the data is incorporated into a master database that can be accessed by a plurality of drivers 101.

The device described herein allows for continuous monitoring of the slope of the torque curve (i.e., d(tau)/d(theta)), allowing the driver 101 to notify the surgeon when an unsatisfactory state such as stripping has occurred, or when the screw may be improperly placed anatomically. Therefore, it is adapted to the potential failure of the driver 101 to prevent such an occurrence. When the surgeon is notified that an unsatisfactory state has occurred, the surgeon can take additional surgical precautions, such as replacing or adding screws, or can initiate patient protection measures, such as instructing protected weight bearing after surgery. These additional precautions can improve surgical outcomes and reduce morbidity for patients, and can increase confidence for the surgeon.

Additionally, in various embodiments, the algorithms used to predict the torque limit or the stopping point for advancement of the screw do not require a predefined torque ratio limit with or without a predetermined safety factor. The torque limit can be modified based on the variation in state as the screw is driven into the bone, and the real time, repeated measurements of the current state and determination of bone properties will provide a real-time updated calculation or prediction of the desirable state as the fastener is inserted. The algorithm or algorithms can be both predictive and adaptive, with adaptations being made based on the differences between the prediction and the actual measured torque/twist curve as data is accumulated, leading to improved accuracy. Proportional-integral-derivative control style algorithms provide a sophisticated predictive and adaptive capability.

Determination of Reference Data

In various embodiments, reference data, reference criteria, and/or other reference values may be used for ascertaining a state of the current procedure. In various embodiments, reference data may be obtained from one or more of: (a) a prior procedure performed on the current patient; (b) a prior procedure performed at a similar anatomical location on the current patient; (c) a prior procedure performed at the same anatomical location on the current patient; (d) a prior procedure performed on another patient; (e) a prior procedure performed on another patient at a similar anatomical location to the location of the current procedure; (g) a procedure performed on a cadaver; (g) a procedure performed on tissue isolated from a cadaver; (h) a prior procedure performed on another patient; (i) a procedure performed on tissue isolated from a non-human; (j) a model of tissue parameters (e.g., density, modulus, stiffness, yield strength, etc.); (k) data obtained about a patient's tissue (e.g., data obtained via x-rays, ultrasound, magnetic resonance imaging, biopsy, blood test, etc.); (l) a simulation of a procedure; (m) a computer simulation of a procedure; and/or from any other source or method.

For example, in various embodiments, a fastener may be driven into the bone of a cadaver for a bone analogous to the bone that is the subject of the current procedure. Measurements may be taken by the driver in use on the cadaver bone. These measurements may be correlated with observed results, such as yielding, stripping, or other bone damage. From such correlations, one or more reference values may be determined such that the reference values can be used as a basis for inferring the state of a current procedure (e.g., whether stripping has occurred in the current procedure).

As another example, reference data may be obtained from prior procedure performed on the current patient. If it was determined, for example, that a certain value of torque was applied to a fastener just prior to a decrease in a slope of torque versus twist, then this applied value of torque may serve as a reference value for the maximum torque that should be applied in the present procedure.

As another example, reference data may be obtained about a bone parameter. For example, data may be obtained about a bone density (e.g., about the patient's bone density; e.g., about the typical bone density for the type of bone involved in the current procedure). A mathematical model may then be used to calculate criteria for determining a state of a current procedure. For example, the bone density may be multiplied by constant to derive a threshold value of applied torque beyond which a fastener should not be driven. As will be appreciated, other calculations, mathematical models, and/or derivations may be used. Other inputs may be used as well, such inputs possibly including fastener characteristics (e.g., fastener diameter, thread density, etc.).

In various embodiments, data from a given procedure may be recorded. Such data may be stored for future use as reference data and/or for determining reference data. Data from a current procedure may be stored in a centralized database (e.g., a database accessible by one or more physicians, hospitals, research agencies, etc.) Data may be tagged, indexed, and/or otherwise associated with various values, such as patient age, gender, health, etc. Data may be anonymized. For example, data may include no personally identifying information, and/or may include a unique code which is nonetheless not directly tied to the patient's personal or identifying information.

Figure 4:
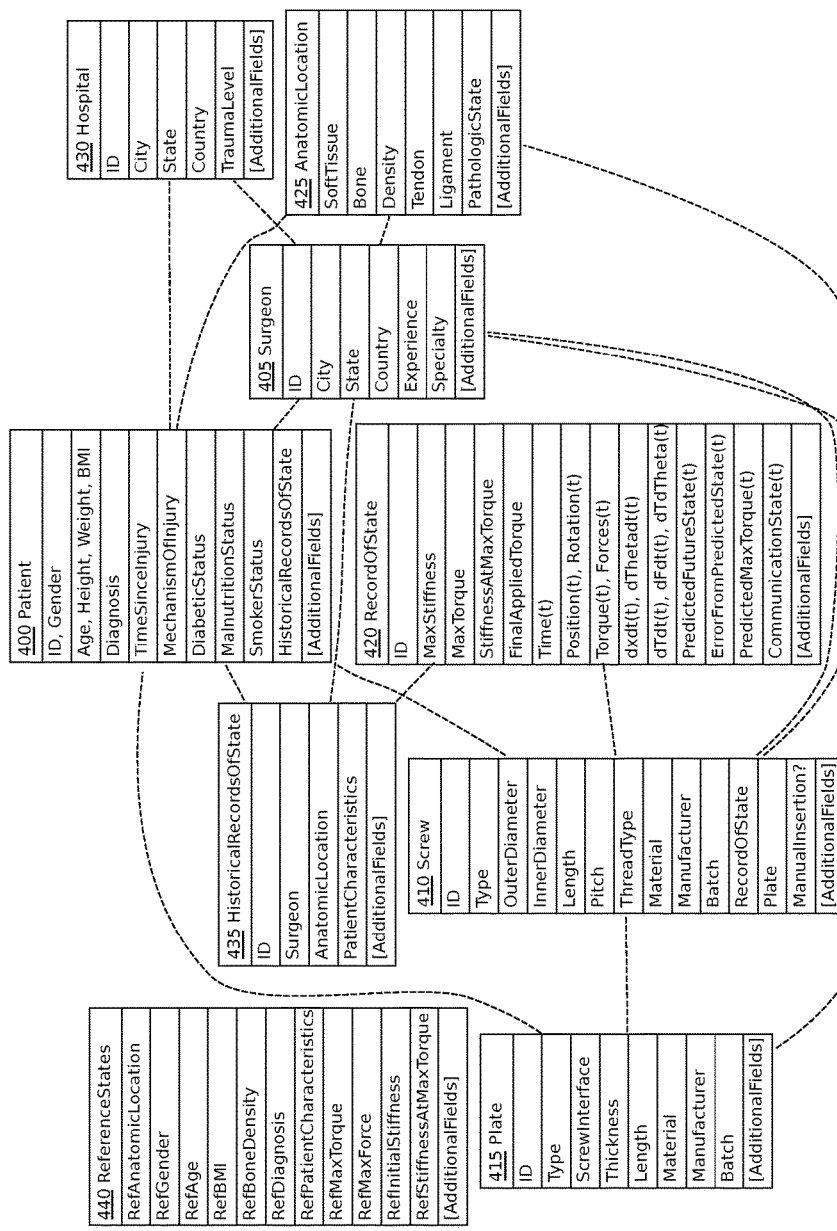
FIG. 4 is a depiction of a data structure according to some embodiments.

FIG. 4 illustrates a data structure that may be used to record data for one or more procedures according to various embodiments. Data may be stored in one or more tables. The tables may be associated with one another through common data entries, fields, keys, and/or other commonalties. The data structure may take the form of a relational database, in various embodiments. In various embodiments, other data structures may be used. Various embodiments contemplate the use of any suitable or appropriate data structure for storing data from a procedure. Although FIG. 4 does not depict actual values for the indicated fields, various embodiments contemplate that such values would be stored. Values may include, for example, "56" for a patient's age, and "Female" for a patient's gender, etc.

Table 415 stores information about a Plate that may be used in a procedure. The table may include descriptors and features of the plate, such as its ID, Screw Interface, Thickness, etc. Table 410 stores information about a fastener or screw that may be used in a procedure. The table may include descriptors and features of the screw, such as an ID, Type, Outer Diameter, Inner Diameter, etc.

Table 420 stores information pertaining to the state of a procedure. The state may include various measurements that have been taken during the course of a procedure and which may represent a state of the procedure during or after the time of measurement. Exemplary measurements may include a position of the fastener, a rotation of the fastener, a torque applied to the fastener, etc. For any given type of measurement (e.g., torque), multiple measurements may be taken. Measurements may be taken at a two or more points in time. Measurements may also be taken by two or more different sensors. Any such measurements may be stored in table 420. In various embodiments, table 420 may store derived or summary statistics, such as a maximum stiffness or maximum torque from among the measurements taken so far. In various embodiments, table 420 may store predictions, inferences, or other deductions made in the course of a procedure. For example, the driver may periodically make predictions of a future measurement, of a maximum torque that will be measured in the future, of a state that will be reached in the future (e.g., that yielding will occur), or of any other future occurrence. These predictions may be recorded in table 420. Table 420 may also store determinations of errors made in predictions (e.g., the degree to which predicted measurements differed from actual measurements).

Table 405 stores information about a surgeon. The surgeon may be the surgeon performing the procedure, assisting with the procedure, or otherwise involved. Fields may include an ID, city of residence, state of residence, name, specialization, years of experience performing surgeries, etc. As will be appreciated, additional tables may be used, in various embodiments, to store information about other medical professionals who might be involved with the procedure.

Table 425 stores information about an anatomic location. The anatomic location may be the location where the current procedure is taking place. The anatomic location may include an indication of the soft tissue, bone, tendon, ligament, or other part involved. Table 425 may also store various characteristics of the anatomic location, including characteristics known beforehand and/or measured during the procedure. Characteristics may include a density (e.g., bone density), pathological state (e.g., cancer), etc.

Table 440 depicts reference data according to some embodiments. Reference data may include data gathered from individuals or populations of individuals. Such data may include data from related patients (e.g., patients with similar age, gender, condition, etc.), from related procedures (e.g., from procedures in the same anatomical location, e.g., from procedures employing the same techniques), or otherwise related or otherwise of possible interest. Reference data may be useful in that data from a current procedure may be compared to the reference data to ascertain the state of the current procedure. For example, a current torque measurement may be compared against a reference max torque in order to determine whether the current procedure is still within an acceptable range of torques.

Table 435 depicts historical records of state. Table 400 may be similar to table 420 as to the types of data it stores. However, table 400 may store data from prior procedures (e.g., as opposed to the current procedure). As will be appreciated, however, tables 400 and 420 need not necessarily contain the same types of data, the same fields, etc.

Table 400 depicts patient information, including an ID, Gender, Age, etc.

Table 430 depicts hospital information, including ID, location, trauma level, etc. As will be appreciated, various embodiments may include tables for non-hospital medical offices, or for any other location where a procedure might be carried out.

FIG. 5 depicts, according to various embodiments a table such as table 420, with representative data values. Row 505 may include measurements taken at various times, such as at times spaced at intervals of one tenth of one second. Corresponding to each time measurement, there may be a measurement of theta (e.g., of degrees through which a fastener has turned), a measurement of pitch (e.g., the pitch of the driver), a measurement of yaw (e.g., the yaw of the driver), an x, y, and z position (e.g., of the driver with respect to a reference coordinate system), etc. Row 501 includes a record of the maximum stiffness (e.g., the slope of torque vs. twist) recorded so far in the procedure, row 502 includes a record of the maximum torque recorded so far, etc. It will be appreciated that, in place of row 517, various additional rows and/or fields may be included in the table.

At row 518 is depicted a communication state. This may store a record of what communications have been outputted or otherwise transmitted to an operator (e.g., to a surgeon). A signal to "continue" may instruct the surgeon to proceed with the advancement of the fastener, since the driver may be inferring that the current state of the procedure is normal. A signal of "warning" may instruct the operator to proceed more slowly, proceed with caution, and/or stop according to the operator's discretion. The signal may be output upon an inference by the driver that the procedure is nearing the point where significant further advancement of the fastener risks incurring undesired damage. A signal to "stop" may instruct the operator to cease the advancement of the fastener. The signal may be output upon an inference by the driver that the procedure has reached a point where further advancement of the fastener will likely cause undesired damage. As will be appreciated, various other communications, signals or outputs may be used, and these may be worded differently without departing from the contemplated embodiments. As will be appreciated, various other states or indications may be represented with the communications.

As will be appreciated, the specific types of data, fields, and arrangements of data depicted in FIGS. 4 and 5 are not intended to be limiting. Various embodiments contemplate the use of additional types of data, fields, tables, etc. Various embodiments contemplate the omission of any one or more fields, tables, types of data, etc., depicted in FIG. 4. Various embodiments contemplate data being arranged in a different order and/or distributed differently among the tables. Various embodiments contemplate more or fewer measurements being taken.

Determining Current States

In various embodiments, it may be desirable to determine a current state or situation of a procedure for which the driver is in use. For example, a driver may be in use for a surgical procedure. It may be desirable to determine whether the procedure is proceeding normally, whether an unexpected situation has occurred, and/or whether an undesirable situation has occurred. In various embodiments, it may be desirable to determine whether a state or situation has been reached such that a new action or change of course would be desirable. For example, it may be desirable to determine whether a fastener has been advanced to such a point beyond which there is a disadvantageous risk/benefit ratio that undesirable damage to tissue may occur. In various embodiments, it may be desirable to determine what stage within an anticipated progression of stages a current procedure is in. For example, it may be desirable to determine whether a fastener is still only partially inserted into a bone, or whether the fastener has been fully inserted and is now beginning to compress the bone. Based on a determination of the current situation, various actions may be taken. Such actions may include, for example, alerting an operator of the driver, halting further advance of the driver, retracting the driver, and/or any other suitable action.

A current state may be determined or inferred from a set of measurements, e.g., from one or more measurements. These measurements may include measurements that have been taken during a procedure. Measurements may be used to derive other quantities. E.g., two or more measurements of torque at different times may be used to determine a slope or derivative of torque as a function of time.

Measurements, and/or derived quantities may be compared to one or more quantities, patterns, criteria, or other metrics that are associated with particular situations. For example, a slope of torque with respect to twist of 1 Newton-meter per radian may be associated with a normal procedure. Thus, for example, if a measured slope of torque versus twist is 1 Newton-meter per radian or within 5% of this value, then the current situation may be classified a normal procedure. However, a slope of 0.3 Newton-meters per radian may be associated with a situation whereby a driver has entered soft tissue, and thereby has entered an incorrect anatomical location. Thus, for example, if a measured slope of torque versus twist is 0.3 Newton-meters per radian or within 5% of this value, then the current situation may be classified as a situation where the driver has entered an incorrect anatomical location.

In various embodiments, the driver may, at various times, determine a current situation of a procedure. The determination may be made based on a set of measurements that have been taken during the procedure. Measurements used may include all prior measurements, or a subset of measurements. For example, measurements used may include measurements taken over a recent time interval (e.g., over the last 500 milliseconds). For example, measurements may include the most recent two measurements of a particular type. Measurements may include measurements taken when some condition was in place (e.g., when the driver was in motion, when the driver was moving the fastener forward, and/or any other relevant condition.) Measurements used may include measurements from a particular sensor or type of sensors. E.g., measurements from torque sensors may be used.

The determination as to the current state of the procedure may be made once, periodically, upon request (e.g., upon request by an operator of the driver), upon the occurrence of some triggering condition (e.g., upon momentary cessation of the forward motion of the driver), or according to any other schedule or criteria.

In various embodiments, a current state or situation of the procedure may be determined by comparing the measurements with criteria (e.g., predetermined criteria) associated with one or more possible states of a procedure. Possible states may include one or more of: (a) the procedure is proceeding normally; (b) the fastener has entered into an incorrect anatomical location; (c) the fastener has entered abnormal tissue; (d) the fastener has entered diseased tissue; (e) the fastener has encountered an inanimate object; (f) the fastener has encountered another fastener; (g) the fastener has advanced to a point to a point beyond which potential risks of further advancement would outweigh potential benefits of further advancement; (h) the fastener has advanced to a point at which the fastener has already inflicted unintended damage; (i) the fastener has advanced to a point at which the fastener has already caused bone stripping; (j) the fastener has advanced to a point of causing bone yield; (k) the fastener has engaged some but not all of its threads with the tissue; (l) the fastener has engaged all of its threads with the tissue; (m) the fastener head has made contact with the tissue or with an object being affixed to the tissue (n) the fastener has begin to cause compression the tissue, or any other possible state.

It will be appreciated that the aforementioned descriptions of states of a procedure are not limited to the precise wording of such descriptions, but are intended to cover conceptually the state being described. It will be appreciated that various embodiments similarly contemplate alternate wordings for the various states described herein.

In various embodiments, after measurements have been compared to criteria associated with one or more possible states, it may be determined which state the current procedure is in. For example, it may be determined that the set of measurements used match the criteria for a first state, but not for any other state, and therefore it may be determined that the current procedure is in the first state.

In various embodiments, measurements may match criteria associated with two or more states. In such cases, a state may be chosen that exhibits the greatest degree of matching, overlap, etc., between the measurements and the criteria for that state. For example, measurements may match the criteria for a first state to a first degree, and may match the criteria for a second state to a second degree, where the second degree is greater than the first degree. Accordingly, it may be determined that the procedure is in the second state.

In various embodiments, a single state of the current procedure may not be determined. Rather, multiple possible states may be determined. For example, if it is determined that measurements match criteria for both a first state and a second state, then both states may be noted. For example, the driver may output an indication that the current procedure may be in the first state or may be in the second state. In some embodiments, the driver may indicate the current procedure may be in both states.

In various embodiments, the driver may indicate a confidence, likelihood, or other metric indicative of the degree or amount by which measurements match the criteria of a given state. For example, the driver may indicate that there is a 60% chance that the current procedure is in a first state. A metric may be determined for more than one state. For example, a driver may indicate that there is a 50% chance that the procedure is in a first state, a 30% chance that the procedure is in a second state, and a 20% chance that the procedure is in a third state. A metric need not be indicated in a numeric fashion, but may be indicated as a color (e.g., with darker colors indicative of a greater degree of matching), a section of a graph (e.g., a pie-chart may indicate the likelihood of two or more states by the size of slices associated with each state), or via any other means.

FIG. 6 depicts various plots of torque versus twist for certain possible states, situations, and/or scenarios that may occur during a procedure. Twist may represent the angle, or number of turns with which a fastener has been driven. Twist may be measured in turns, rotations, degrees, radians, or other suitable quantity. In various embodiments, twists may be measured in terms of the number of threads of a fastener that have entered a tissue, that have passed a certain point, and/or that have met any other criterion or criteria. As depicted in FIG. 6, twist is represented by the variable "theta", representing the number of degrees through which the fastener has been turned.

Torque may represent the amount of torque experienced by a fastener throughout a procedure as it is increasingly driven into a tissue. In a real-world scenario, a fastener may or may not be driven through as many turns as are depicted in FIG. 6. Therefore, for example, a plot of a real world scenario will not necessarily show a complete curve analogous to one of those depicted in FIG. 6. Rather for example, a plot of a real world scenario may just show a curve that is analogous to a first half, first third, leftmost half, or other portion of a curve such as one of those depicted in FIG. 6.

Plots depicted in FIG. 6 may represent maximum values of torque measured at certain twists. For example, if two or more measures of torque are taken at a given twist, the relevant measurement to compare to FIG. 6 may be the larger measurement of the two torques. In various embodiments, FIG. 6 may represent values of torque measured while a driver is actively operating in the forward direction. Thus, for example, a torque measured while a driver is idle may not be appropriate to compare to one of the plots depicted in FIG. 6. However, in some embodiments, it may be appropriate to compare any measured torque at a given twist to those depicted in the plots of FIG. 6, regardless of which direction the driver was operating in.

In various embodiments, certain features of the various plots shown in FIG. 6 may serve as hallmarks, benchmarks, evidence, clues, or other distinguishing features used to determine a state, situation, and/or scenario of a current procedure. Exemplary distinguishing features may include a slope of torque versus twist, a sudden or rapid change of slope of torque versus twist (e.g., a corner or "elbow" that appears in the plot), a change of slope of torque versus twist, a decrease in slope of torque versus twist, a number of twists for which the plot proceeds at substantially the same slope, and/or any other feature of the plot.

As indicated by the legend in FIG. 6, plots are shown representing an "ideal" or normal procedure, an "incorrect anatomical location" plot representing a situation in which a fastener has advanced into a tissue or other place where it was not intended to go, and a "pathologic tissue" plot representing a situation where the fastener has advanced into pathologic tissue, such as unhealthy or otherwise compromised tissue. Point 600 lies on an initial leg of a plot that corresponds to both the "ideal" and "incorrect anatomical location" scenarios. In various embodiments, at point 600, a fastener has not completely advanced into tissue and its head has not come in contact with a plate or with the tissue itself.

Accordingly, there is a gradual increase in torque versus twist (theta) as more and more threads of the screw come into contact with the tissue.

Point 600 may be contrasted with point 620, which lies on an initial leg of a plot corresponding to advancement of the fastener into "Pathologic Tissue". Pathologic tissue may exhibit greater weakness, pliability, reduced stiffness, and/or any other characteristic that may contrast with normal tissue. Accordingly, a lesser torque may be observed as the fastener advances into pathologic tissue as compared to normal tissue. Further, the slope of torque versus twist may be lower than that exhibited by a fastener entering normal tissue. In various embodiments, only a minimal level of torque (e.g., zero torque) may be measured as a fastener enters pathologic tissue.

Thus, according to various embodiments, the tissue into which a fastener is being advanced may be classified as normal, if one or more of the following are measured: (a) there is a positive value of torque measured as the fastener begins to enter the tissue; (b) the slope of measured torque versus twist is positive as the fastener enters the tissue. According to various embodiments, tissue may be classified as pathologic if one or more of the following are measured: (a) the torque is zero or near zero even as the fastener enters the tissue; (b) the slope of torque versus twist is zero or near zero as the fastener enters the tissue; (c) the torque remains zero or near zero for some predetermined range of theta (e.g., for 300 degrees; e.g., for a range of theta corresponding to the twist required to make contact between the head of the fastener and the tissue).

In various embodiments, as theta increases following point 600, the plots for "Idea" and "Incorrect Anatomical Location" may reach a point at which there is a rapid increase in torque. This may correspond to a phase where the head of the fastener has made contact with the plate (or tissue), and now tightening is occurring. As theta reaches a value just prior to points 605 and 615, the two plots may diverge. At point 605, tightening continues to occur consistent with normal tissue and/or a normal procedure, and torque continues to rise rapidly. However, at 615, torque has leveled off as a function of theta. This may occur because the fastener may advanced into an anatomic location where the tissue does not give it the same "purchase" or "bite" or strength of thread contact with surrounding tissue. For example, an incorrect anatomic location may represent soft tissue, non-bone tissue, a cavity, a sac, or any other tissue, location or surroundings.

Thus, according to various embodiments, a procedure may be classified as normal or ideal, if one or more of the following are measured: (a) there is a rapid increase in measured torque as a function of twist (e.g., theta); (b) there is a large positive slope in measured torque as a function of twist; and (c) the large positive slope of torque versus twist continues for some predetermined amount of twist (e.g., for at least 100 degree). According to various embodiments, a procedure may be deemed to have reached an "incorrect anatomical location" if one or more of the following are measured: (a) there is an increase in measured torque versus twist followed by a leveling off of torque versus twist, at which point torque remains relatively constant as a function of twist; (b) there is an increase in measured torque versus twist followed by a leveling off of torque versus twist, at which point torque increases more gradually as a function of twist; (c) a large positive slope in measured torque versus twist endures for less than a predetermined amount of twist (e.g., for less than 100 degree).

Although not explicitly depicted in FIG. 6, in various embodiments, the "ideal" and "incorrect anatomical location" scenarios may diverge earlier, possibly before there is a steep increase in the slope of torque versus twist. For example, the fastener may advance into an incorrect anatomical location even before the head of the fastener has made contact with the bone. In such a scenario of reaching the incorrect anatomical location, there may be an initial leveling off of even the gradual slope on the leg where point 600 lies. When the head of the fastener does make contact, there may be exhibited an increase in slope of torque versus twist. This slope may or may not be as steep as is the slope for the ideal scenario following contact by the head of the fastener.

Thus, according to various embodiments, a procedure may be deemed to have reached an "incorrect anatomical location" if one or more of the following are measured: (a) there is gradual increase in measured torque versus twist followed by a leveling off of torque versus twist; (b) there is a leveling off of measured torque versus twist followed by a significant increase in measured slope of torque versus twist where, however, the significant increase results in a slope that is still less than a predetermined slope (e.g., less than a predetermined slope that would be expected in an ideal scenario).

In various embodiments, a current procedure may be classified as having reached an "incorrect anatomical location" if a slope of torque versus twist is not within an appropriate tolerance level (e.g., is not positive, e.g., is not greater than a threshold value). In various embodiments, a current procedure may be classified as having reached an "incorrect anatomical location" if the approximate ratio of slope (i.e., of torque versus twist) to max load (i.e., the highest torque measured) is not within a particular tolerance (i.e., is more than a certain value). This classification may be effective because, for a given slope of torque versus twist, an "ideal" procedure may exhibit a higher max load than does a procedure where the fastener has reached an incorrect anatomical location. Thus, the ratio of slope to max load may be higher in a procedure with an incorrect anatomical location than with a normal or "ideal" procedure.

As with the "Ideal" and "incorrect anatomical location" scenarios, the "pathologic tissue" scenario may exhibit an increase in the slope of torque versus twist. Point 625 lies on a portion of the plot where this increase is visible. This increase may also occur when the head of the fastener has come into contact with the fastener or tissue. However, in contrast to the slope exhibited with the other two depicted scenarios, the slope for the "pathologic tissue" scenario may be more gradual (e.g., may be less than a predetermined value).

Thus, according to various embodiments, tissue may be deemed "pathologic" if there is measured a significant increase in slope of torque versus twist (e.g., the increase is greater than a first predetermined amount), but that such resultant slope is less than a second predetermined value.

In various embodiments, point 605 may represent a desirable time to stop the advancement of the fastener in the course of a normal or ideal procedure. In practice, with respect a current procedure underway, an operator may not have the benefit of viewing the entire extent of the plots depicted in FIG. 6. Thus, various embodiments described further herein and below include ways of determining when a desirable stopping point has been reached. Various embodiments may include (a) stopping once a predetermined or computed torque value has been met or exceeded; (b) stopping once there have been a predetermined or computed amount of twist applied to the fastener; (c) stopping once there has been a predetermined or computed amount of twist applied the fastener (e.g., 180 degrees) following the point at which measured torque begins to increase rapidly, etc.

At point 610, the procedure will be approaching a maximum possible torque value (e.g., given the properties of the tissue, type of screw, etc.). At this point, the tissue may exhibit yielding. It may be desirable to provide an indication that a point of maximum possible torque is approaching and/or that yielding is occurring. In such circumstances, it may be desirable to stop the advancement of the fastener.

As depicted at 610, there may be a gradual decrease in the slope of torque versus twist, although the slope may still remain positive, and the slope may still remain relatively steep. Also, at 610, the measured value of torque may be relatively high (e.g., may have exceeded a particular or predetermined value). Also at 610, fastener may have been turned through some significant number of degrees, amount of twist, etc., since the large increase in slope of torque versus twist. Thus, according to various embodiments, a procedure may be classified as having reached a point of yielding and/or a point of maximum torque if one or more of the following are measured: (a) a decrease in a slope of torque versus twist; (b) a (a) a decrease in a slope of torque versus twist where the slope still remains positive; (c) a decrease in a slope of torque versus twist where decrease is less than a certain amount; (d) a number of turns of the fastener since the steep increase in slope of torque versus twist has exceeded some particular or predetermined value (e.g., the number of turns has exceeded 200 degrees); (e) measured torque has exceeded a predetermined or particular value (e.g., 800 Newton millimeters; e.g., 200 Newtons multiplied by the screw diameter; etc.).

In various embodiments, as theta increases significantly past point 610 in the "ideal" case, there may be a rapid fall off in measured torque. This may correspond to bone stripping. Thus, in various embodiments, a procedure may be classified as having reached a point of stripping, having exceeded the twist at which max torque has been reached, and/or related concept, if one or more of the following occur: (a) there has been a decrease in measured torque as twist has increased; (b) the slope of torque versus twist has decreased; (c) the slope of torque versus twist has become negative; (d) the slope of torque versus twist has decrease by more than a predetermined amount (e.g., by more than 5 Nmm per degree); (e) the measured value of torque has decreased below a certain threshold (e.g., below 800 Nmm); (f) the slope of torque versus twist has become negative with more than a predetermined magnitude (e.g., with a magnitude greater than 10 Nmm per degree).

In various embodiments, if a procedure has been classified as reaching a point of stripping, a point of structural failure, or other similar or related scenario, then a remediation may be indicated. A driver may output a signal to an operator and/or to a remote computer indicative of a remediation. Exemplary remediations might include redoing the procedure with a larger screw, redoing the procedure at another location, and/or any other appropriate remediations.

In various embodiments, procedures involving an incorrect anatomical location or pathologic tissue may also reach points of maximum torque and/or points of stripping. In such cases, there may be exhibited a decrease in measured torque, a decrease in slope of torque versus twist, a negative slope of torque versus twist, and/or a measured torque that is below a certain level.

It will be appreciated that the plots depicted in FIG. 6 represent just some possible sets of reference plots, or reference data that may be used as a basis for comparison. Various embodiments contemplate the use of other reference plots and/or other sets of reference data. For example, reference data may include quantities that are mathematically related to the quantities depicted in FIG. 6. Such quantities may include force, angular velocity, acceleration, derivatives of torque versus twist, and/or any other type of reference data. Also, in various embodiments, reference data need not be mathematically related to the data illustrated in FIG. 6.

It will be appreciated that, in various embodiments, not all data, values, etc., from plots illustrated in FIG. 6, or from any other FIG., need be used as a basis for comparison. For example, in various embodiments, measurements taken during a real-world procedure may be compared to a single reference slope of torque versus twist.

It will be appreciated that plots depicted in FIG. 6, and other reference data, may represent data under certain assumptions. The assumptions may include assumptions about a diameter of a fastener, a number of threads of a fastener, a thread pitch for a fastener, a material of a fastener, a type of bone, health of bone, etc. In various embodiments, reference data may be scaled and/or otherwise altered to account for differences in assumptions behind the reference data and realities of the current procedure. For example, if a fastener used in a current procedure is twice the diameter of an assumed fastener used in deriving reference data, then the reference measures of torque may be multiplied by a scale factor of 2 prior to comparison to measurements taken during a current procedure. Alternatively, in various embodiments, data taken from a current procedure may be scaled or otherwise altered so as to be comparable to the reference data.

Various embodiments need not use reference data in graphical form. For example, reference data may include a quantity or set of quantities that are not necessarily plotted or graphed. Measurements taken during a procedure may be compared in some way to the reference data in order to determine a state or possible state of the current procedure.

Figure 8:
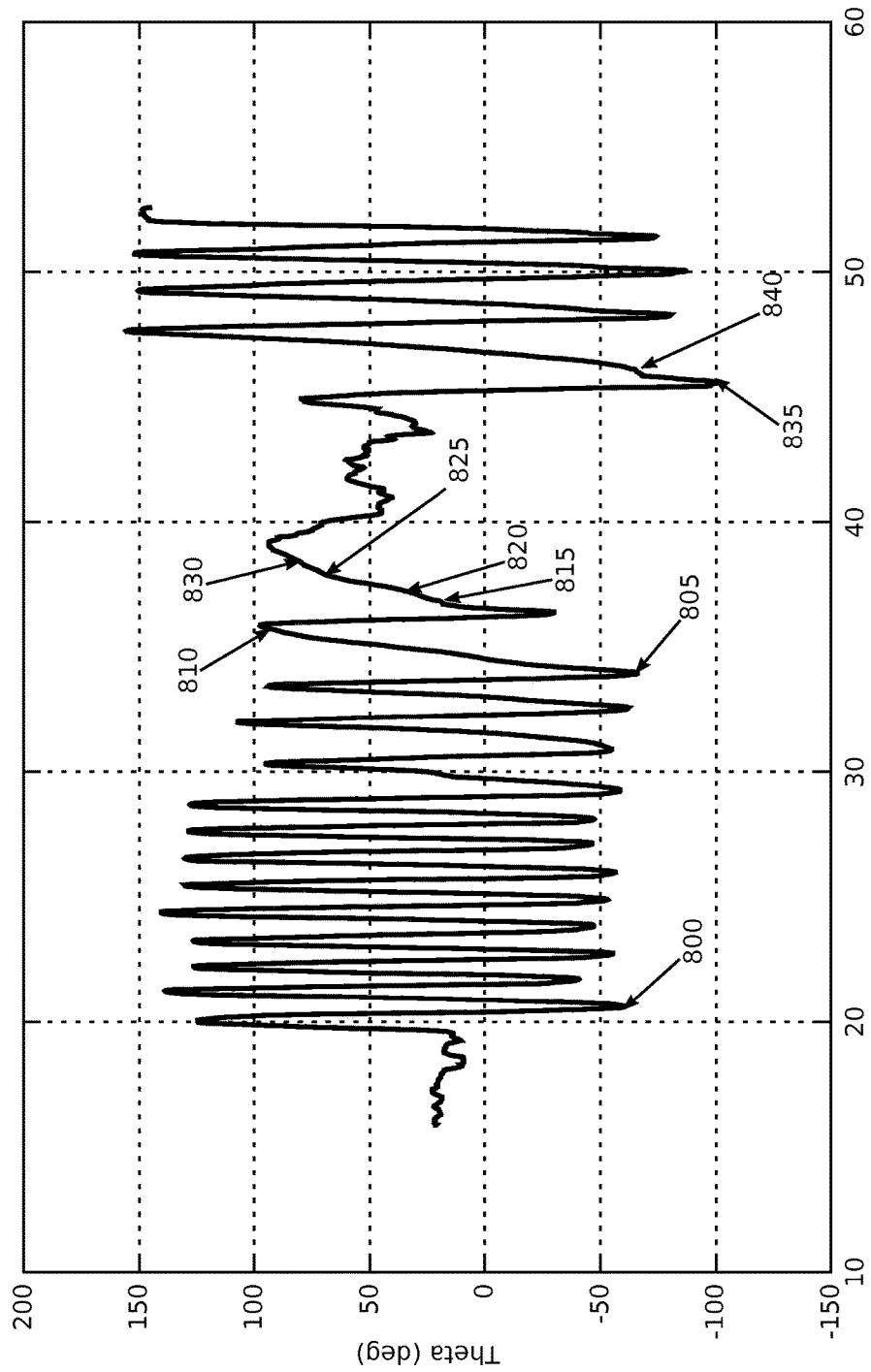
FIG. 8 is a graphical representation of a measured twist with respect to time during insertion of a screw into tissue, according to various embodiments.
Figure 9:
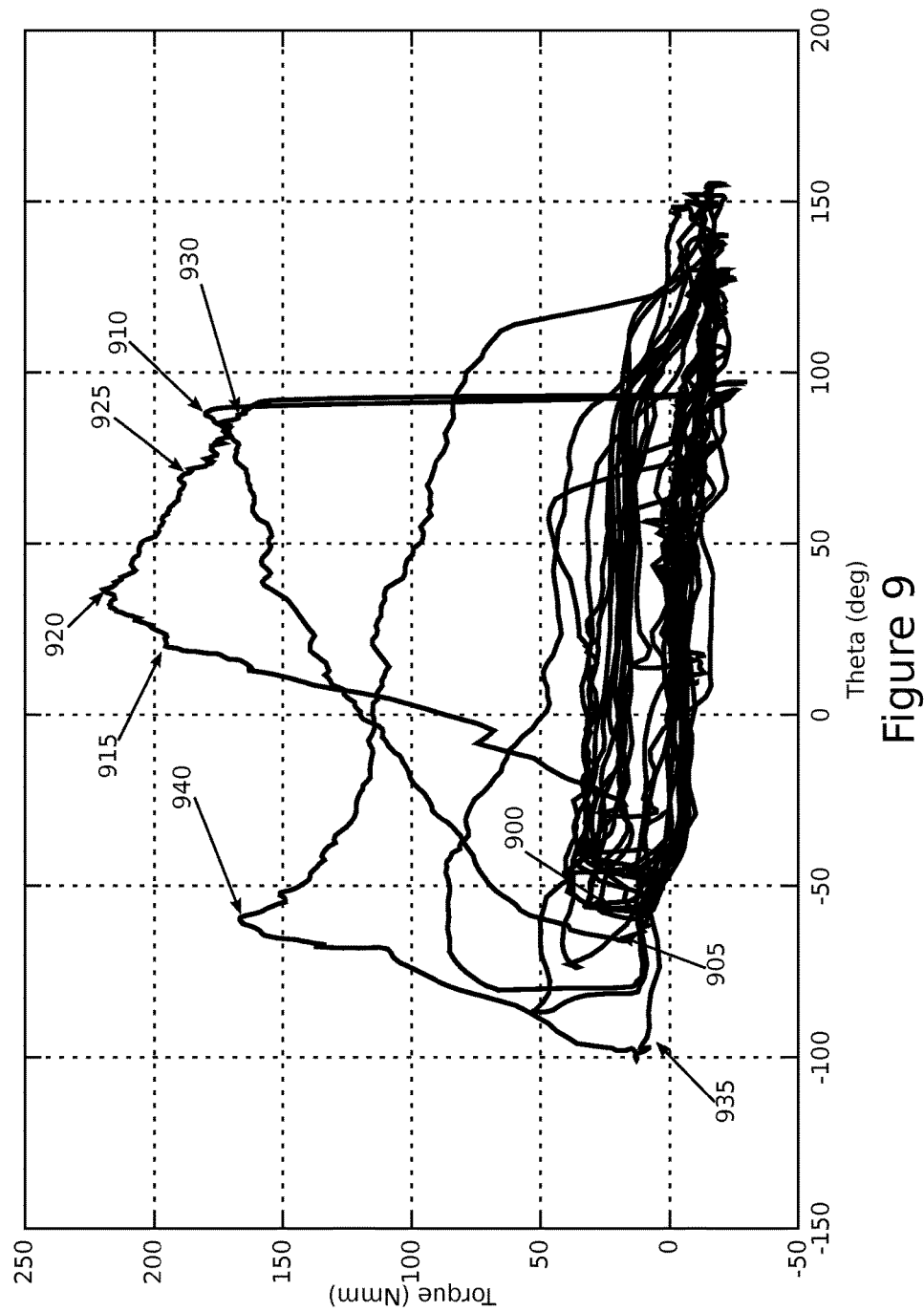
FIG. 9 is a graphical representation of a measured torque with respect to twist during insertion of a screw into tissue, according to various embodiments.

FIGS. 7-9 illustrate exemplary plots of various measurements as might occur during a procedure. Each plot may be representative of the same procedure, but with different measurements illustrated. Each plot may provide a different perspective as to the current state of the procedure. Each plot may provide a basis for making deductions, inferences, and/or predictions about the current state of the procedure and/or about future measurements and/or states of the procedure.

In various embodiments, plots such as those illustrated in FIGS. 7, 8, and 9 may be available to an operator in real-time or substantially real time. In various embodiments, plots such as those depicted in FIGS. 7, 8, and 9 may be viewable simultaneously by an operator (e.g., on the same display screen; e.g., on two or more displays screens). The operator may have the ability to customize the display of the plots, which plots are displayed, or any other factor. In various embodiments, the operator may expand the size of one plot relative to another, zoom in on a plot, indicate a range of values to be shown on the plot (e.g., a range of x-axis values; e.g., a range of y-axis values), indicate colors in which data will be shown, indicate a scale that will be used, and/or provide any other instruction. The operator may control the display of plots in various ways, such as by using voice control, gestures, an input device, a mouse, a keypad, a touch screen, and/or via any other method.

As will be appreciated, the illustrated plots represent only some possible means of showing data visually, and are not intended to be limiting. Various embodiments contemplate other means of providing data visualizations. Various embodiments contemplate plots with different sample rates, different scales (e.g., linear, log, etc.; e.g., different minimum and maximum values illustrated), different units (e.g., seconds, milliseconds, etc.), different axis labels, different grid spacings, labels of individual data points (e.g., labels of local or global maximum values, etc.) etc. In various embodiments, plots may be shown with one or more modifications applied to raw data. Such modifications may including smoothing algorithms (e.g., plots of moving averages), confidence intervals, color codings (e.g., data above a certain value is colored in a different way than data below such value), etc.

FIG. 7 illustrates an exemplary plot of torque as a function of time, as might occur during a procedure. The plot exhibits a somewhat periodic nature in that torque fluctuates up and down in a somewhat regular pattern for at least a portion of the plot. This periodic nature of the plot may be attributable to the periodic motion of an operator's wrist. Namely, the operator may alternately rotate his wrist in a first direction to advance the fastener, then rotate his wrist in the other direction to reposition his grip, then once again rotate his wrist in the first direction, etc. Note the that, in various embodiments, the operator need not actually let go of the handle of the driver when rotating his wrist in the reverse direction. The ratchet mechanism, according to various embodiments, may allow the operator to maintain his grip such that rotations of the wrist in one direction drive the fastener forward, but rotations of the wrist in the other direction do not engage the fastener and allow the fastener to maintain its position without being retracted.

At the time noted by 700, the operator has begun to advance the fastener into the tissue. For some period of time thereafter (approximately 12 seconds), the maximum measured torque values increase very gradually, on average. At the time noted by 705, the fastener head has engaged with the plate (i.e., the plate being fastened to the patient's bone tissue for therapeutic reasons). At this point there is a sudden increase in stiffness and measured torque increases rapidly. At time 710, the operator turns his wrist in the backwards direction (i.e., turns the ratchet backwards). This may represent the first back-turn during a "stiff" cycle.

At the time noted by 715, there is a distinct change in slope of the plot of torque versus time. Namely, there has been a distinct decrease in slope even as the slope is still positive. In various embodiments, at this point in time, the driver may cause a message to be output to the operator. In various embodiments, the message may indicate that the operator should observe caution in proceeding, should slow the rate of fastener advancement, or should stop advancing the fastener. As will be appreciated, the message may be output using any suitable form (e.g., visual, audio, haptic), and may be output using any suitable wording or visual indicator (e.g., color, stop sign, etc.).

At the time noted by 720, the maximum torque capacity of the bone has been exceeded. Beyond this time, measured torque begins to decrease, and the slope of torque versus time becomes negative. At the time noted by 725, there has been a steady trend of decreasing torque with time, even as the fastener has continued to advance. This may be a clear indication that undesired damage has been caused to the tissue.

At the time noted by 730, advancement of the fastener is terminated by the operator. For some time thereafter, there is a pause in activity, during which measured torque is close to zero. During this period of time, the operator may be considering next steps. At the time noted by 735, the operator has restarted advancement, perhaps to verify that damage has occurred. In various embodiments, the operator may already intend to take remedial action, so additional damage incurred by further advancement of the fastener might be acceptable. At the time noted by 740, a second local maximum torque is identified. This local maximum is lower than the earlier local maximum identified at 720, thus confirming that undesirable damage has occurred. Beyond the time noted by 740, additional turns of the fastener continue to damage the bone. In this case, in various embodiments, a likely remedial action is to remove the screw and replace it with one with a larger thread diameter.

With reference to FIG. 8, a plot from the same procedure is shown, except that now measured theta is plotted as a function of time, rather than torque. Measured theta may correspond to the number of degrees through which the handle of the driver has been turned with respect to some reference value (e.g., with respect to some arbitrary "zero" value). As indicated above, a ratchet mechanism built into the driver, according to some embodiments, may allow theta to decrease even while the driver remains engaged with the fastener, and while the fastener itself is not retracted. According to various embodiments, times noted by 800, 805, 810, 815, 820, 825, 830, 835, and 840 correspond to the same times noted by 700, 705, 710, 715, 720, 725, 730, 735, and 740.

With reference to FIG. 9, a plot from the same procedure is shown, except now measured torque is plotted as a function of measured theta. As was evident from FIG. 8, the same values of theta were often reached many times as the operator alternately turned his wrist one way and then the other. Accordingly, in FIG. 9, it is evident that, for a given value of theta, multiple measurements of torque may be plotted (i.e., the plot is not necessarily one-to-one).

According to various embodiments, times noted by 900, 905, 910, 915, 920, 925, 930, 935, and 940 correspond to the same times noted by 700, 705, 710, 715, 720, 725, 730, 735, and 740.

By plotting torque versus theta, rather than versus time, certain states may become visually clearer. Further, the shape of the plots may take a more standard or typical form that is not so dependent on the pace, mannerisms, or physical characteristics of an individual operator. In other words, for example, a plot of torque versus theta would be expected to take more or less the same form regardless of how quickly the operator decides to drive the fastener.

In various embodiments, a plot such as that depicted in FIG. 9 presents a graphical representation of stiffness, any change in stiffness, and current and past torque values. It thus graphically presents data useful for interpreting the current state of the procedure. It also thusly presents data useful for planning the ongoing procedure and for anticipating future outcomes or for reacting to adverse states.

In various embodiments, a plot such as that depicted in FIG. 9 may be compared to one or more reference plots, such as those depicted in FIG. 6, in order to determine a current state and/or predicted future state of a procedure.

In various embodiments, a plot of a current procedure (e.g., a procedure in progress) such as that depicted in FIG. 9 may be shown with one or more overlays or other indicators. Overlays may represent reference values or ranges. For example, one or more plots such as those shown in FIG. 6 (and/or one or more of the portions thereof), may be superimposed on a plot of the current procedure. In this way, an operator may be able to visualize how measurements from the current procedure track measurements depicted in a reference plot. In various embodiments, an overlay may depict a range of reference values (e.g., a range of possible values of torque for a given theta). This range may be shown in a translucent color, for example. If a plot of the current procedure falls within the range, then an operator may infer that the current procedure is in a state corresponding to that shown by the corresponding reference plot.

In various embodiments, it may be desirable to provide an indication of the time at which various data points shown in FIG. 9 were measured. In various embodiments, it may be desirable to provide an indication of the temporal progression of data points shown in FIG. 9. For example, it may be desirable to indicate which data points were measured at proximate points in time to one another. In this way, for example, an operator may ascertain trends or trajectories within the data. As another example, it may be desirable to indicate which data points were measured most recently. With a ready indication of recent data points, an operator may more readily ascertain a current state of the procedure. Temporal indications may be provided using color coding (e.g., more recently sampled data may be shown in warmer colors), using shading (e.g., more recently sampled data may be shown darker colors) in via a shape of plot points (e.g., circles, squares, x's, etc.), via explicit time labels (e.g., the time at which a data point was measured may be superimposed on the plot by the data point), or via any other means.

In various embodiments, only data extending back for a predetermined amount of time may be shown. For example, only data extending for the prior 10 seconds may be shown. In various embodiments, only a predetermined number of the most recent data points may be shown (e.g., only the last 1000 data points; e.g., only the last 500 data points). Showing only a limited number of data points, for example, may allow an operator to focus on the most current and/or most relevant data.

In various embodiments, data may be shown if it meets certain criteria. For example, data may be shown that represents a local maximum in torque versus theta. Also, data measured within a certain time interval of a local maximum may be shown (e.g., for context).

In various embodiments, a plot of torque versus theta may be shown in such a way that turns of the driver handle in one direction (e.g., in the reverse direction) are not counted. For example, when the driver is being turned in the reverse direction (e.g., as determined by a measured decrease in theta), data points may not be plotted. This may reduction in plotted data points may increase the clarity of a plot such as that of FIG. 9, in some embodiments.

In various embodiments, a plot of torque versus theta may be shown in such a way as to measure turns of the fastener itself. In this case, theta may range over values greater than those representing the capabilities of a human wrist to turn in a single motion. In various embodiments, theta may range over values representing more than one complete turn (i.e., 360 degrees), and may range in values representing multiple complete turns (e.g., theta may range over 3600 degrees, 7200 degrees, etc.). In various embodiments, to create such a plot, reverse turns of the handle may be ignored, and measured increases in theta during forward turns of the handle may be added to the highest value of theta previously used during the prior forward turn of the handle. For example, during a first forward turn of the handle, the handle may reach a maximum theta value of 125 degrees, with a measured torque of 10 Nmm. Data points up to and including the value (125 degrees, 10 Nmm) may be plotted. The handle may then be turned in the reverse direction, ultimately reaching a theta value of −55 degrees. Data points may not be plotted during the reverse turning of the handle. Then, the handle may be turned in the forward direction again. At this point, a measured theta of −54 degrees may be plotted as a value of 126 degrees, a measured theta of −53 degrees may be plotted as a value of 127 degrees, etc. In this way, a plot may be become a one-to-one plot. Further, the plot may allow for greater clarity and interpretability, according to some embodiments. As will be appreciated, various embodiments contemplate this and other ways of display data including torque versus theta and/or any other data.

Normal Procedure

In various embodiments, measurements of torque may be taken. Such measurements may be taken periodically, or according to any other schedule or interval spacing, as will be appreciated. Measurements may be taken by a driver, or by other suitable device.

In various embodiments, certain measurements may be indicative of, and/or interpreted as, a normal procedure. That is, for example, certain measurements may be expected during the course of normal procedure. In various embodiments, a hallmark of a normal procedure is a gradual and substantially linear increase in measured torque as the number of turn of the fastener. Thus, a normal procedure may be characterized by a slope of torque versus twist that remains within a certain range over a certain number of turns. The normal or expected range for torque versus twist may be, for example 0.1-0.15 Newton-meters per radian. As will be appreciated, a normal or expected range may be characterized in other fashions, such as via a single value together with a tolerable variation from this value (e.g., 0.125 plus or minus 0.025 Newton-meters per radian).

In various embodiments, the extent to which a slope of torque versus twist remains substantially the same may be another indicator of a normal procedure or not. For example, if the slope remains the same over up to 10 full turns of the fastener, then this may be indicative of a normal procedure. However, in various embodiments, if the slope remains the same for too long (e.g., for more than 10 full turns of the fastener), then this may be indicative of a problem, abnormal procedure, etc. The extent to which the slope is expected to remain substantially the same may depend on various factors, including the length of the fastener (e.g., longer fasteners would expect to result in the slope remaining substantially constant for a greater number of turns), the number of threads on the fastener (e.g., fasteners with more threads would expect to result in the slope remaining substantially constant for a greater number of turns), and any other factors.

Normal Procedure; Indications to Stop Driving

In various embodiments, if torque exceeds a certain threshold (e.g., 3 Newton-meters; e.g., 2 Newton-meters), then it may be determined that the fastener has been inserted to a sufficient degree that risks of driving the fastener further outweigh potential benefits. In other words, it may be determined that the potential benefits of a possible stronger hold by the fastener are outweighed by the increasing risk of undesirable damage to the tissue should the fastener be driven any further. Such risks may include risks of stripping, yielding, or other risks. In various embodiments if torque exceeds a certain threshold, then it may be determined that the fastener should not be driven further.

Various embodiments described herein have used a measure of torque as a function of screw rotation in order to classify a procedure, tissue state, and/or to generate recommendations or other signals for an operator. In various embodiments, measures of applied force may be employed as means for classifying, making inferences, or making deductions. In various embodiments, applied force as a function of twist may be used. In various embodiments, it may be assumed that measured force would be proportional to measured torque. Thus, similar criteria for classification may be used for measured force as those criteria for classification used for measured torque. For example, a rapid fall-off in measured force may be indicative of bone stripping, etc.

In various embodiments, a force measuring screw may be employed. The screw may measure a force differential from one end of the screw to the other. The measured force differential may be used as a means for classification, inference, and/or recommendation.

In various embodiments, a slope of torque versus twist may increase for increasing theta, even when the slope may already be high. This increase may be attributable, for example, to contact with another foreign object, such as another fastener or plate. Thus, in various embodiments, upon detection of an increase in torque versus twist, a signal, output, alert, or other indication may be provided. For example, the driver may output a message indicative of an abnormal state, indicative of possible contact by the fastener with another foreign object, or indicative of any other explanatory phenomenon.

In various embodiments, torque may be measured periodically, on a regular basis, and/or according to any other schedule. If torque exceeds a certain threshold, then there may be allowed only a predetermined amount of further twist (e.g., an additional 720 degrees of twist). Presumably, the allowable amount of twist may bring the driver to a desirable state of high torque with minimal risk of causing damage.

Predictions

In various embodiments, the driver may periodically (or according to any other schedule) measure slope of torque as a function of screw turns. Using the plurality of measured states or any subset of states, the driver may predict a subsequent measurement or set of measurements (e.g., the next set of measurements). The predictions may lead to several actions by the driver, such as the issuance of a "use caution" or "stop turning" signal if the prediction is for a decrease in torque or slope.

In various embodiments, a given measurement may be compared to a value that had been predicted for that same measurement. Thus, for a given prediction, an error may be determined (e.g., subsequently determined once the actual value is measured). Similarly, for a given measurement, a prediction error may be determined by comparing the actual measurement to a value that had been predicted for that measurement.

The measurement data set thus includes a prediction error for subsequent measurements, said error may be incorporated for subsequent predictions. For example, if a recently determined prediction error for a measurement of torque was −20 Nmm, then a value of −20 Nmm may be added to a future prediction of torque. As will be appreciated, some function of a prediction error (e.g., the prediction error multiplied by a constant) may be used for making future predictions. If the prediction errors are above a threshold value, the driver may issue a warning which instructs caution or a directive to stop advancing the screw.

In one non-limiting example, the driver measures a linear slope of torque vs. degrees of turn. It further predicts an ongoing linear torque response with increasing degrees of turn up to a certain number of degrees of turn or up to a certain torque value. Those degrees of turn may be 180 or any other number of degrees of turn or the torque value may be 1000 Nmm or any other torque value. The prediction may depend on the measured slope and other known conditions such as screw diameter. The driver subsequently measures a decrease in slope with increasing twist prior to the set degrees of turn or set torque, i.e., a prediction error has been found. After reaching a threshold, this error is recognized as a likely onset of plasticity and the driver issues new guidance to limit twist to less that 180 degrees or torque to less than 1000 Nmm. The new guidance may be 90 degrees or 500 Nmm where presently the driver is at 80 degrees and 400 Nmm. Subsequent measurements may cause additional refinements in guidance. Refinement may include "stop turning" or "undesired damage is likely to have occurred" where the slope remains lower than predicted or becomes negative. Refinement may include "continue turning" if the slope returns to a previous level, thus indicating a likely insignificant anomaly in tissue property or sensor measurement. The predicted response may be based on polynomial fits, exponential fits, logarithmic fits, trigonometric fits, or other mathematical functions or look-up tables. The predicted response may be based on combinations of these or other mathematical functions or other look-up tables. Repeated predictions, at periodic intervals, may be used to further refine the accuracy and integrity of the prediction.

In the various embodiments, "periodically" may indicate time periods, degrees of turn, increments of torque, or any other measure. As will be appreciated, periodically may include the case of "continuous" measurement where the high frequency of measurement exceeds the ability of the user to perceive the discrete period. "Continuous" periodic measurement may indicate time increments which are shorter than any dynamic time scale relevant to the turning of the fastener.

Direct Determination of Output without Determination of a State

In various embodiments, a driver may determine or generate an output without making a determination of a state of a procedure. For example, a driver may generate as an output a statement that says "Stop drilling", or "Drill for only one more half turn of the driver", or "Bone stripping has occurred", or any other statement. Such outputs may be generated, in various embodiments, without any explicit determination of state.

In various embodiments, an output may be determined in a similar manner to the way a state may be determined. In various embodiments, a criterion or set of criteria may be associated with a particular output. If the measurements taken during a procedure satisfy the criteria, then the associated output may be determined, generated, emitted, transmitted, or otherwise utilized. For example, the driver may cause a computer screen to display the output.

Ratchet

Various embodiments include a ratchet, which provides a mechanism which decouples the two ends of the shaft while the one end turns in one direction but not while it turns in the other direction. In various embodiments, the ratchet may make it easier to drive fasteners because the operator needn't remove a hand from the driver. Rather, the operator cycles back and forth, but the fastener's end of the shaft only goes in one direction.

Cycling the Driver to Measure Data

In various embodiments, a driver may be operable to proceed in either a forward or reverse direction. When proceeding in a forward direction, the driver may cause a fastener to advance or go deeper into tissue. When proceeding in a reverse direction, the driver may cause a fastener to recede, or come out of the tissue. As will be appreciated, a "forward" direction may represent one direction of rotation (e.g., clockwise), while a "reverse" direction may represent another direction of rotation (e.g., counter-clockwise).

In various embodiments, measurements may be taken when the driver is operating in the reverse direction. For example, the driver may measure the torque experience by the fastener as the driver is operating in the reverse direction.

In various embodiments, when a driver operates in a reverse direction, it may cause the fastener to retrace a position, degree of twist, or other physical state, or other state, that it has already occupied. For example, when operating in the reverse direction, a driver may cause a fastener to be situated such that it is only halfway into a bone tissue. The driver may have previously been in the same situation where it was halfway into the bone tissue. The driver may have later been driven further such that it was three quarters of the way into the bone tissue, before being retracted to the point where it was again only halfway into the bone tissue. As another example, a fastener may have previously been driven past five twists into bone tissue, all the way to six twists, before being pulled back to five twists again.

In various embodiments, operating a driver in a reverse direction may allow the recording of additional measurements that can be useful for determine a state of the procedure. In various embodiments, measurements obtained when the driver operates in reverse may be compared to measurements obtained for a similar situation of the fastener when the driver had been operated in the forward direction. For example, over the course of a procedure, a first torque measurement may be taken at 5 twists of the fastener while the driver operates in the forward direction, and then a second torque measurement may be taken at 5 twists of the fastener while the driver operates in the reverse direction.

Comparison of two or more analogous measurements (e.g., measurements taken at a similar situation of the fastener) from times when the driver was operating in both forward and reverse directions (or in multiple forward or multiple reverse direction cycles separated by an opposite direction cycle) may be used to determine a state of a procedure. In various embodiments, if the two measurements are the same, or substantially similar (e.g., differing by less than 5%, e.g., differing by less than 10%), then it may be determined that the procedure is in a normal state. Exemplary measurements that may be compared from the forward and reverse directions of operation may include torque, slope of torque versus twist, and angular velocity. In various embodiments, if the two measurements are different (e.g., differing by more than 10%), then it may be determined that the procedure is not in a normal state. For example, it may be determined that bone stripping or other undesirable damage to tissue has occurred.

In various embodiments, operation of a driver in a reverse direction may advantageously allow for the obtainment of one or more additional measurements without risking undesirable damage to tissue. For example, when a driver is operated in a reverse direction, the fastener is presumably not carving out any more bone tissue, nor increasing compressive forces on bone, but is rather retracing a bore hole that has already been made, and moving away from the bone.

In various embodiments, a driver may automatically initiate operations in the reverse direction. The driver may initiate such reverse operations if it determines that additional measurements may be desirable; if it determines that a current state of the procedure is inconclusive (e.g., if prior measurements do not precisely match criteria associated with known possible states; e.g., if prior measurements match criteria associated with more than one state); if it determines that such measurements would give greater confidence to a determine of the current state of the procedure; if it determines that there may have been errors in prior measurements; if it determines that there was an excessively wide variation in prior measurements (e.g., if there has been a high amount of noise in prior measurements); if it determines that prior measurements are lacking; or for any other reason.

In various embodiments, a driver may output a signal requesting that an operator of the driver operate the driver in the reverse direction. For example, the driver may output a tone of a particular frequency, may cause an associated display to show a text message saying "Please reverse the driver momentarily in order to better gauge the bone state", may cause the output of a message via synthetic voice, or may otherwise signal the operator to reverse the direction of the driver.

Comparison of two or more dissimilar measurements (e.g., measurements taken at substantially dissimilar situations of the fastener) from times when the driver was operating in both forward and reverse directions (or in multiple forward or multiple reverse direction cycles separated by an opposite direction cycle) may be used to determine a state of a procedure. In an exemplary embodiment, if indications of damage have been observed at a high torque, the driver may instruct a reversal in order to acquire the slope at a lower torque. If the subsequent slope at the lower torque is different (e.g., differing by more than 10%) from the slope at the higher torque, then it may be determined that the procedure is not in a normal state. Similarly, if the subsequent slope at the lower torque is different (e.g., differing by more than 10%) from the slope at similar torque level at an earlier time, then it may be determined that the procedure is not in a normal state. For example, it may be determined that bone stripping or other undesirable damage to tissue has occurred. In these examples, if the slopes are similar (e.g., differing by less than 10%), then it may be determined that the procedure is in a normal state.

Displaying Graphs of the Measurements

In various embodiments, sensor readings, measurements, derived quantities, determine states, alerts, messages, and/or any other data or information may be output. Such data or information may be output in various sensory modalities, including via sound, display, vibrations, haptic feedback, olfactory means, or via any other means.

In various embodiments, data may be shown as a time series plot. For example, a plot may show measured torques as function of time. In various embodiments, data may be shown as a plot of any two or more types of quantities. For example, a plot may be shown of measured torque as a function of the twist of the fastener.

In various embodiments, data may be plotted in the form of two-to-one or many-to-one functions. For example, if the driver is operated in reverse, then multiple measurements may be taken as a function of the same twist or rotation of the driver. For example, at five twists of the driver, there may be plotted measurements of 2 Newton-meters (e.g., as measured when the driver operated in the forward direction) and 3 Newton-meters (e.g., as measured when the driver operated in the reverse direction).

In various embodiments, displayed or plotted data may be color coded or otherwise coded according to various schemes. For example, a yellow color along a portion of a plot may indicate that the procedure has reached a point of high risk at the time such measurements were taken. A red color may indicate that damage had been done at the time such measurements were taken. In various embodiments, color coding or other coding may also be used to easily distinguish different types of data. E.g., blue may indicate torque measurements, while green may indicate velocity measurements. As will be appreciated, various embodiments contemplate the use of other colors, other coding schemes, and other manners of displaying data.

Measurements

In various embodiments, one or more measurements may be taken. The measurements may be taken during a procedure, such as during the insertion of a screw into bone tissue. The measurements may be taken by the driver. The measurements may be taken using one or more sensors that make up the driver. Thus, in various embodiments, measurements may include sensor readings. The measurements may be used to gauge a state of the procedure, such as whether the procedure is proceeding normally, whether damage has occurred to the tissue, whether the driver has encountered an incorrect anatomical location, etc.

Measurements may represent or be indicative of a kinetic quantity. A kinetic quantity may include a quantity that describes energy, work, or related concept. An exemplary kinetic quantity is the elastic energy stored in a compressed tissue at a given point in time during a procedure.

Measurements may represent or be indicative of a kinematic quantity. A kinematic quantity may include a quantity that represents position, motion, trajectory, velocity, acceleration, or related concept. An exemplary kinematic quantity is the angular velocity of a fastener.

Measurements taken may represent or be indicative of one or more of (a) a twist; (b) a torque; (c) an acceleration; (d) a velocity; (e) an angular velocity; (f) a compression of tissue; (g) a quantity of stored elastic energy; (h) an amount of work performed; (i) a displacement; (j) a force; (k) a tension of tissue; (l) a normal strain; and (m) a shear strain. Measurements may also include derivatives of any of the aforementioned items. Derivatives may be taken with respect to time, position, twist, or with respect to any other suitable quantity. Measurements may include first derivatives, second derivatives, or any level of derivative of the above quantities. Measurements may include partial derivatives of any of the above quantities. Measurements may include integrals of any of the above quantities. Measurements may include any mathematical transformation, transformation, approximation, numerical approximation, discretization, quantization, interpolation, or other function of any of the above quantities and/or of any sensor readings.

Exemplary measurements may describe the number of turns that a fastener has undergone (e.g., a twist measurement), the torque that is experienced by a fastener, an angular velocity of a fastener, a position of a fastener, a relative position of a fastener, an amount of compression of a bone, an amount of strain energy stored in a bone, a force applied to a fastener, etc.

In various embodiments two or more measurements may be taken simultaneously, or substantially simultaneously. The measurements may be averaged or otherwise combined to determine a summary measurement. For example, two different torque sensors may each simultaneously measure a torque. The readings from the sensors may be averaged to determine a summary torque measurement at that point in time.

In various embodiments, two or more measurements taken at different times may be averaged or otherwise combined to determine a summary measurement.

In various embodiments, an approximation to a derivative may be determined and may then be used, e.g., to determine a state of the procedure. An approximation to a derivative may be determined, for example, by taking the difference between two measurements, and dividing by the elapsed time that occurred between when the two measurements were taken. As will be appreciated, other methods may be used for approximating derivatives and are contemplated for various embodiments described herein.

Sensors used to take measurements may include torque sensors, position sensors, continuous position sensors, inertial measurement units, gyroscopes, pressure sensors, strain gauges, axial strain gauges, shear strain gauges, and any other sensors.

In various embodiments, measurements may be taken at various points in time. Measurements may be taken at regular time intervals. Measurements may be taken at irregular time intervals. Measurements may be taken periodically, such as every ten milliseconds. Measurements may be taken upon some triggering condition. For example, torque measurements may be taken once the driver has been set in motion.

In various embodiments, measurements may be stored, such as in a memory of the driver. One or more measurements may be stored in compressed formats. In various embodiments, measurements may include various descriptive information, such as a time of the measurement or a sensor that was used to take the measurement.

Determining a Tissue Property

In various embodiments, a mechanical property (e.g. a modulus) of tissue (e.g., of bone) may be ascertainable from measured data (e.g., data measured during a procedure, e.g., data measured prior to a procedure). One non-limiting example of a mechanical property of tissue is its modulus. The property may be related to the slope of one or more plots or curves relating two measurable quantities. An exemplary curve is a curve of torque versus twist (e.g., theta). The exemplary relationship may hold because the measured torque presumably comes as a result of strain and deformation (where the relationship between strain and stress depends on the modulus) of the bone as the screw is forced through it. The slope may also be or become dependent on damage or its absence, where damage is a function of modulus and material strength or plasticity. Slope presumably also depends on friction, which is dependent on the interacting materials (e.g., screw and bone) and their surfaces and the lubrication between them. The exemplary relationship also depends on the screw features (e.g., diameter, thread, pitch) and whether the hole is pre-drilled or not. For a given known situation (thread, pre-drill, etc), the presumably strongest torque dependencies are most likely modulus and friction. In various embodiments, the friction coefficient may be assumed to remain constant. Thus, slope has largest dependence on modulus (of the unknowns). Thus, from slope a modulus can be inferred even if not calculated directly.

An exemplary formula that may be used for deriving Modulus is as follows:

$$\tau = c_2 \times \text{Modulus} \times \mu \times (\theta - c_1).$$

In the formula, c1 and c2 are assumed to be known constants, mu (a friction coefficient) is assumed known based on the given circumstances of the procedure, and constant in relation to the other variables. Tau indicates the torque on a fastener, and theta indicates the degree to which the fastener has turned. This equation may be solved for Modulus based on as little as two data points of tau and theta (e.g., using standard techniques for systems of linear equations). As will be appreciated, however, additional data points may be used to reduce any possible deleterious effects of noisy data. In various embodiments, the above formula may be used directly or in any equivalent or transformed state. For example, one or more algebraic transformations may be made to the formula. As another example, the formula may be differentiated with respect to theta, and measured or derived slopes of tau versus theta may be plugged in for the derivative of tau with respect to theta.

According to various embodiments, any formulas described herein, and any variations on such formulas may be used (e.g., by the driver; e.g., by a remote computer) to solve for a mechanical property of tissue. The mechanical property of tissue may then be used in the current procedure, and/or may be stored for future reference in a subsequent procedure.

In various embodiments, another formula may be used. In the exemplary relationship, this variation of formula may also account for axial force (along the screw axis) as well as thread properties.

$$\tau = c2 \times \text{Modulus} \times \text{mu} \times (\theta - c1) + F \times \text{mu} \times c3 + c4 \times (\theta - c5)$$

In the above, mu is a friction coefficient, and F is an axial force, i.e., the force from the driver head as it is pushed into the fastener along the fastener axis.

Constant c3 accounts for the fact that the axial force is not normal to the thread surfaces, thus, both axial and transverse force components combine as a surface normal force which multiplies by the friction coefficient to generate friction and torque. Note also that constants c2 and c3 are dependent on the screw geometry (including its pitch and its inner and outer diameters which are related to the local moment arm of the resulting frictional shear stresses). Lastly, constant c4 accounts for the fact that damage/work may be occurring as the screw advances. For instance, if there is no pre-drilled hole, work must be done drilling and tapping the hole with the screw as the screw advances. This exemplary formula may likewise be solved for modulus in standard fashion, such as by using systems of linear equations with two measured data points for tau and theta.

Various embodiments of finding a mechanical property of tissue contemplate the use of additional formulas. Such formulas may be non-linear with respect to torque and other factors. One non-limiting example may account for the variation of axial force along the axis of screw. Another non-limiting example may account for the variation in one or more other properties by assumption of spatially varying functions for these properties. Examples of spatially varying properties include friction, modulus, and other properties. These examples may require the integration of differential equations of force and moment equilibrium. Various embodiments contemplate the use of discrete numerical methods such as the finite element method for computing modulus from the previously described torque, stiffness, and other measurements.

Other Documents Incorporated by Reference

U.S. Pat. No. 4,359,906, entitled "Device and Method for Inserting a Bone Screw", and issued Nov. 3, 1982, is hereby incorporated be reference herein for all purposes.

U.S. patent application number 2014/0222012, entitled "Smart Screw-Driver for Preventing Inadvertent Screw Stripping in Bone", and published on Aug. 7, 2014, is hereby incorporated by reference herein for all purposes.

Automation and Self Driving

In various embodiments, the driver 101 may be automated, or self-driving, with the algorithm determining when the driver 101 will stop inserting the fastener. The self-driving mechanisms of the driver may be electrical motors, solenoids, pneumatics, hydraulics, or any other form of mechanical actuation.

Embodiments

The following are embodiments, not claims:

Embodiment T. A device for driving a fastener into tissue, comprising:
  a handle having a first end and a second end;
  a shank, extending from the first end of the handle and terminating in a head;
  a continuous position measurement device operably coupled to the device;
  at least one torque sensor is operably coupled to the device; and
  at least one of an indicator or a transmitter to transmit a signal to a secondary device having an indicator, is operably coupled to the continuous measurement device and the torque sensor.

Embodiment U. A method of driving a fastener into a tissue with a driver, comprising the steps of:
  recording a previous state of the driver at $t_0$, including a first torque measurement and a first position measurement;
  detecting a current state of the driver at $t_1$, including a second torque measurement and a second position measurement;
  predicting mechanical properties of a patient's tissue based on the previous state and the current state;
  predicting an optimal torque measurement based on the previous state and the current state; and
  determining whether the predicted optimal torque measurement has been reached based on the second torque measurement.

Embodiment V. The method of Embodiment U, further comprising the step of:
  determining whether the tissue has started to strip, based on the previous state and the current state.

Embodiment W. The method of Embodiment U, further comprising the step of:
  Stopping, reversing, or cycling the driver to obtain additional states.

Embodiment X. The method of Embodiment U, wherein a plurality of previous states of the driver are recorded in a historical record, and wherein the historical record and the current state are used to predict the mechanical properties of the patient's tissue and to predict the optimal torque measurement.

Embodiment Y. A method of advancing a fastener into a tissue with a driver, comprising the steps of:
  recording a previous state of the driver at $t_0$, including a first torque measurement and a first position measurement;
  predicting a predicted future state of the driver at $t_1$, including a second torque prediction and a second position prediction based on an optimal anatomic location for the fastener and the previous state;

detecting a current state of the driver at $t_1$, including a second torque measurement and a second position measurement;
comparing the predicted future state and the current state to determine whether the fastener is advancing as predicted; and
notifying a user if the fastener is not advancing as predicted.

Embodiment Z. The method of Embodiment U, further comprising the step of: Stopping, reversing, or cycling the driver to obtain additional states.

In various embodiments, sensor readings may be taken when the driver and/or fastener is receding from the tissue. In various embodiments, sensor readings may be taken when the driver is operating in the reverse direction.

Embodiment F. A device for driving a fastener into tissue, the device comprising:
a handle having a first end and a second end;
a shank extending from the first end of the handle and terminating in a head; one or more sensors;
an output device; and
a processor, in which the processor executes instructions to:
receive a first set of readings from the one or more sensors during a first interval when the fastener is receding from the tissue; and
cause the output device to output a first signal indicative of the first set of readings.

Embodiment F.2 The device of embodiment F in which the first signal encodes a graphical representation of the first set of readings.

In various embodiments, it may be determined based on the first set of readings that no unintended damage has occurred yet. This may be conveyed via an output signal.

Embodiment F.0 The device of embodiment F, in which the processor further executes instructions to:
determine based on the first set of readings that the fastener has not previously advanced to a point of causing unintended damage; and
cause the output device to output a second signal based on the determination that the fastener has not previously advanced to a point of causing unintended damage to the tissue.

Embodiment F.0.1 The device of embodiment F.0 in which the processor further executes instructions to:
receive a second set of readings from the one or more sensors during a second interval when the fastener is advancing into the tissue,
in which, in determining that the fastener has not previously advanced to a point of causing unintended damage, the processor executes instructions to compare the first set of readings to the second set of readings.

Embodiment F.0.1.1 The device of embodiment F.0.1 in which, in determining that the fastener has not previously advanced to a point of causing unintended damage, the processor executes instructions to:
compare the first set of readings to the second set of readings; and
determine that the first set of readings is similar to the second set of readings.

Embodiment F.0.1.1.1 The device of embodiment F.0.1.1 in which the first set of readings are representative of a first amount of friction encountered when the fastener is receding from the tissue, and the second set of readings are representative of second amount of friction encountered when the fastener is advancing into the tissue.

Embodiment F.0.1.1.2 The device of embodiment F.0.1.1 in which the first set of readings are representative of a first amount of torque encountered when the fastener is receding from the tissue, and the second set of readings are representative of second amount of torque encountered when the fastener is advancing into the tissue.

Embodiment K. A device for driving a fastener, the device comprising:
a handle having a first end and a second end;
a shank extending from the first end of the handle and terminating in a head;
a sensor;
an output device; and
a processor, in which the processor executes instructions to:
receive a set of readings from the sensor;
determine, based on the set of readings, a first slope of torque with respect to twist over a first interval, and a second slope of torque with respect to twist over a second interval, in which torque represents torque applied by the device to the fastener, and twist represents twists of the fastener;
determine that the second slope is less than the first slope;
determine a first signal indicative of the second slope being less than the first slope; and
cause the output device to output the first signal.

Embodiment K.1 The device of embodiment K in which the processor further executes instructions to:
determine a first threshold value for torque based on the first slope;
determine a second threshold value for torque based on the second slope;
determine a third value of torque based on the set of readings;
determine that the third value of torque is within a predetermined range of the second threshold value; and
cause the output device to output a second signal indicating that the third value of torque is within a predetermined range of the second threshold value.

Embodiment K.1.1 The device of embodiment K.1 in which the processor further executes instructions to:
determine that the head of the fastener has made contact with a surface; and
cause the output device to output a third signal indicating that the head of the fastener has made contact with the surface.

Embodiment K.1.2 The device of embodiment K.1 in which the processor further executes instructions to:
determine that surrounding tissue has reached a yielding point; and
cause the output device to output a third signal indicating that the surrounding tissue has reached a yielding point.

Embodiment K.2 The device of embodiment K in which the processor further executes instructions to:
determine, based on the first slope, a first number of turns of the fastener required to reach a threshold value for torque;
determine, based on the second slope, a second number of turns of the fastener required to reach a threshold value for torque; and
cause the output device to output a second signal indicating the second number of turns.

Embodiment K.3 The device of embodiment K in which the processor further executes instructions to:

determine, based on the first and second slopes, that the fastener has advanced to a point at which the fastener has already inflicted unintended damage;

determine a second signal indicative of advancement by the fastener to a point at which the fastener has already inflicted unintended damage; and cause the output device to output the second signal.

Embodiment J. A device for driving a fastener, the device comprising:

a handle having a first end and a second end;

a shank extending from the first end of the handle and terminating in a head; one or more sensors;

an output device; and a processor, in which the processor executes instructions to:

receive a first set of readings from the one or more sensors;

determine, based on the set of readings, a second set of quantities representative of the progression of the fastener, in which each of the second set of quantities represent one of a (a) a kinematic quantity, and (b) a kinetic quantity;

determine a first correspondence between: (i) the second set of quantities, and (ii) a first set of criteria indicative of a normal procedure;

determine a second correspondence between: (iii) the second set of quantities, and (iv) a second set of criteria indicative of advancement by the fastener to a point at which the fastener has already inflicted unintended damage;

determine, based on the first and second correspondences, that the fastener has already inflicted unintended damage;

determine a first signal that is indicative of the fastener having already inflicted unintended damage; and cause the output device to output the first signal.

Embodiment J.5 The device of embodiment J in which the processor further executes instructions to:

determine a second signal that is indicative of a remediation step that may be taken by an operator of the device; and cause the output device to output the second signal.

Embodiment J.5.1 The device of embodiment J.5 in which, in determining the second signal, the processor executes instructions to determine a second signal indicative of a remediation step to replace the current fastener with a larger fastener.

Embodiment J.5.1 The device of embodiment J.5 in which, in determining the second signal, the processor executes instructions to determine a second signal indicative of a remediation step to use bone growth hormone.

In various embodiments, a determination may be made as to whether a procedure is in a normal or typical state. In various embodiments, a determination may be made as to whether a fastener has advanced into an incorrect anatomical location.

Embodiment G. A device for driving a fastener, the device comprising:

a handle having a first end and a second end;

a shank extending from the first end of the handle and terminating in a head; one or more sensors;

an output device;

a processor, in which the processor executes instructions to:

receive a first set of readings from the one or more sensors;

determine, based on the set of readings, a second set of quantities representative of the progression of the fastener, in which each of the second set of quantities represent one of a (a) a kinematic quantity, and (b) a kinetic quantity;

determine a first correspondence between: (1) the second set of quantities, and (2) a first set of criteria indicative of a normal procedure;

determine a second correspondence between: (3) the second set of quantities, and (4) a second set of criteria indicative of entry by the fastener into an incorrect anatomical location;

determine, based on the first and second correspondences, that the fastener has advanced into an incorrect anatomical location;

determine a first signal that is indicative of the advancement by the fastener into an incorrect anatomical location; and cause the output device to output the first signal.

Embodiment G.1. The device of embodiment G, in which the second set of quantities includes a measured slope of the torque on the fastener with respect to the twist on the fastener, and in which, in determining the second correspondence, the processor executes instructions to:

compare the measured slope to a reference slope, in which the reference slope is representative of a boundary below which the measured slope would be deemed to satisfy the second set of criteria; and determine that the measured slope is below the reference slope.

Embodiment G.2. The device of embodiment G, in which the second set of quantities includes a set of measured values of torque on the fastener, and in which, in determining the second correspondence, the processor executes instructions to:

determine the maximum torque measured on the fastener from among the second set of quantities;

compare the maximum torque to a reference torque, in which the reference torque is representative of a boundary below which the maximum torque would be deemed to satisfy the second set of criteria; and determine that the maximum torque is below the reference torque.

Embodiment G.3. The device of embodiment G, in which the second set of quantities includes:

a first twist of fastener at a point when measured torque values on the fastener begin to increase by more than a predetermined rate; and a second twist of the fastener at a point when measured torque values on the fastener substantially stop increasing, and in which, in determining the second correspondence, the processor executes instructions to:

determine the difference between the second twist and the first twist;

compare the difference to a reference twist, in which the reference twist is representative of a boundary below which the difference would be deemed to satisfy the second set of criteria; and determine that the difference is below the reference twist.

Embodiment G.4. The device of embodiment G, in which the second set of quantities includes a set of measured values of torque on the fastener and a set of measured twists of the fastener, and in which, in determining the second correspondence, the processor executes instructions to:

determine the maximum torque measured on the fastener from among the second set of quantities;
determine a first twist of fastener at a point when measured torque values began to substantially equal the maximum torque value;
determine a second twist of the fastener at a point when measured torque values on the fastener began to decrease substantially from the maximum torque value, and
determine the difference between the second twist and the first twist;
compare the difference to a reference twist, in which the reference twist is representative of a boundary above which the difference would be deemed to satisfy the second set of criteria; and
determine that the difference is above the reference twist.

Embodiment G.5. The device of embodiment G, in which the processor further executes instructions to cause the first set of readings to be stored in a medical record.

Embodiment G.6. The device of embodiment G, in which the processor further executes instructions to cause the second set of quantities to be stored in a medical record.

Embodiment G.7 The device of embodiment G, in which the processor further executes instructions to:
retrieve a third set of quantities from a medical record of a prior procedure in which an incorrect anatomical location was reached; and
generate the second set of criteria from the third set of quantities.

Embodiment G.7 The device of embodiment G, in which the processor further executes instructions to:
retrieve a third set of quantities from a medical record of a prior procedure in which an incorrect anatomical location was reached; and
generate the second set of criteria from the third set of quantities.

Embodiment G.7.1 The device of embodiment G.7, in which, in generating the second set of criteria, the processor executes instructions to:
determine, based on the third set of quantities, a reference number of twists of a fastener that occurred during the prior procedure in which a measured torque on the fastener was substantially at its maximum value.

Embodiment E. A device for driving a fastener, the device comprising:
a handle having a first end and a second end;
a shank extending from the first end of the handle and terminating in a head;
one or more sensors;
an output device;
a processor, in which the processor executes instructions to:
receive a first set of readings from the one or more sensors;
determine, based on the set of readings, a second set of quantities representative of the progression of the fastener, in which each of the second set of quantities represent one of a (a) a kinematic quantity, and (b) a kinetic quantity;
determine a first correspondence between: (1) the second set of quantities, and (2) a first set of criteria indicative of a normal procedure;
determine a second correspondence between: (3) the second set of quantities, and (4) a second set of criteria indicative of entry by the fastener into an incorrect anatomical location;
determine a third correspondence between: (5) the second set of quantities, and (6) a third set of criteria indicative of entry by the fastener into diseased tissue;
determine a fourth correspondence between: (7) the second set of quantities, and (8) a fourth set of criteria indicative of contact by the fastener with an inanimate object;
determine a fifth correspondence between: (9) the second set of quantities, and (10) a fifth set of criteria indicative of advancement by the fastener to a point beyond which potential risks of further advancement would outweigh potential benefits of further advancement;
determine a sixth correspondence between: (11) the second set of quantities, and (12) a sixth set of criteria indicative of advancement by the fastener to a point at which the fastener has already inflicted unintended damage;
determine a selected correspondence from among the first, second, third, fourth, fifth, and sixth correspondences;
determine a first signal that is indicative of the selected correspondence; and
cause the output device to output the first signal.

Embodiment E.1 The device of embodiment E in which each of the second set of quantities represent one of: (a) a twist; (b) a torque; (c) an acceleration; (d) a velocity; (e) an angular velocity; (f) a compression of tissue; (g) a quantity of stored elastic energy; (h) an amount of work performed; (i) a displacement; (j) a force; (k) a tension of tissue; (l) a strain; (m) a shear strain; (n) a derivative of one of items 'a' to 'm'.

Embodiment E.2 The device of embodiment E in which each of the second set of quantities represent one of: (a) a twist; (b) a torque.

Embodiment E.3 The device of embodiment E in which the output device is a haptic feedback device, and in which, in causing the output device to output the first signal, the processor executes instructions to cause the output device to output a haptic signal.

Embodiment E.6 The device of embodiment E in which, in determining the first signal, the processor executes instructions to:
determine a first tone if the selected correspondence is the first correspondence;
determine a second tone if the selected correspondence is the second correspondence;
determine a third tone if the selected correspondence is the third correspondence;
determine a fourth tone if the selected correspondence is the fourth correspondence;
determine a fifth tone if the selected correspondence is the fifth correspondence; and
determine a sixth tone if the selected correspondence is the sixth correspondence.

Embodiment E.4 The device of embodiment E in which the handle comprises a sealed handle.

Embodiment E.5 The device of embodiment E further comprising:
a power source; and
an inductive charging unit for recharging the power source.

Embodiment H. A device for driving a fastener, the device comprising:
a handle having a first end and a second end;
a shank extending from the first end of the handle and terminating in a head;
one or more sensors;

an output device;
a processor, in which the processor executes instructions to:
receive a first set of readings from the one or more sensors;
determine, based on the set of readings, a second set of quantities representative of the progression of the fastener, in which each of the second set of quantities represent one of a (a) a kinematic quantity, and (b) a kinetic quantity;
determine, based on the second set of quantities, an anatomical location into which the fastener has advanced.

Embodiment D. A device for driving a fastener, the device comprising:
a handle having a first end and a second end;
a shank extending from the first end of the handle and terminating in a head;
a sensor;
an output device; and
a processor, in which the processor executes instructions to:
receive a set of readings from the sensor;
determine, based on the set of readings, a first slope of torque with respect to twist over a first interval, and a second slope of torque with respect to twist over a second interval, in which torque represents torque applied by the device to the fastener, and twist represents twists of the fastener;
determine a first correspondence between: (1) the determined first and second slopes, and (2) a first set of criteria indicative of a normal procedure;
determine a second correspondence between: (3) the determined first and second slopes, and (4) a second set of criteria indicative of entry by the fastener into an incorrect anatomical location;
determine a third correspondence between: (5) the determined first and second slopes, and (6) a third set of criteria indicative of entry by the fastener into diseased tissue;
determine a fourth correspondence between: (7) the determined first and second slopes, and (8) a fourth set of criteria indicative of contact by the fastener with an inanimate object;
determine a fifth correspondence between: (9) the determined first and second slopes, and (10) a fifth set of criteria indicative of advancement by the fastener to a point beyond which potential risks of further advancement would outweigh potential benefits of further advancement;
determine a sixth correspondence between: (11) the determined first and second slopes, and (12) a sixth set of criteria indicative of advancement by the fastener to a point at which the fastener has already inflicted unintended damage;
determine a selected correspondence from among the first, second, third, fourth, fifth, and sixth correspondences;
determine a first signal that is indicative of the selected correspondence; and
cause the output device to output the first signal.

Embodiment D.5 The device of embodiment D in which the selected correspondence is the sixth correspondence, in which the processor further executes instructions to:
determine a second signal that is indicative of a remediation step that may be taken by an operator of the device; and
cause the output device to output the second signal.

Embodiment D.5.1 The device of embodiment D.5 in which, in determining the second signal, the processor executes instructions to determine a second signal indicative of a remediation step to replace the current fastener with a larger fastener.

Embodiment D.5.1 The device of embodiment D.5 in which, in determining the second signal, the processor executes instructions to determine a second signal indicative of a remediation step to use bone growth hormone.

Embodiment D.1 The device of embodiment D in which the first and second intervals are twist intervals.

Embodiment D.2 The device of embodiment D in which the first and second intervals are time intervals.

Embodiment D.3 The device of embodiment D in which the first and second intervals are torque intervals.

Embodiment D.3 The device of embodiment D in which the selected correspondence represents the greatest from among the first, second, third, fourth, and fifth correspondences.

Embodiment D.4 The device of embodiment D in which the selected correspondence represents the most likely from among the first, second, third, fourth, and fifth correspondences.

Embodiment C. A device comprising:
a handle having a first end and a second end;
a shank extending from the first end of the handle and terminating in a head;
a torque sensor operable to measure torque applied by the device to a fastener;
a twist sensor operable to measure the quantity of twists that have been applied to the fastener;
an output device; and
a processor, in which the processor executes instructions to:
receive an indication of a first torque reading taken by the torque sensor at a first time;
receive an indication of a first twist reading taken by the twist sensor at the first time;
receive an indication of a second torque reading taken by the torque sensor at a second time;
receive an indication of a second twist reading taken by the twist sensor at the second time;
determine a first slope of torque with respect to twist based on the indications of the first and second torque readings and based on the indications of the first and second twist readings;
receive an indication of a third torque reading taken by the torque sensor at a third time;
receive an indication of a third twist reading taken by the twist sensor at the third time;
receive an indication of a fourth torque reading taken by the torque sensor at a fourth time;
receive an indication of a fourth twist reading taken by the twist sensor at the fourth time;
determine a second slope of torque with respect to twist based on the indications of the third and fourth torque readings and based on the indications of the third and fourth twist readings;
determine, based on the first and second slopes that an alert criterion has been satisfied; and
cause, based on the determination that the alert criterion has been satisfied, the output device to output an alert.

Embodiment C.1 The device of embodiment C, in which the alert criterion is satisfied if the the second slope differs from the first slope, but does not differ from the first slope by more than an expected percentage.

Embodiment C.2 The device of embodiment C, in which the alert criterion is satisfied if the the second slope is less than the first slope.

Embodiment C.2.1 The device of embodiment C.2 in which, in causing the output device to output an alert, the processor executes instructions to cause the output device to output an indication that a screw has entered an incorrect anatomical location.

Embodiment C.3 The device of embodiment C, in which the alert criterion is satisfied if the the second slope is less than the first slope by more than a predetermined percentage.

Embodiment C.4 The device of embodiment C, in which the alert criterion is satisfied if the the second slope is greater than the first slope by more than a predetermined percentage.

Embodiment C.4 The device of embodiment C further comprising a motor operable to drive rotation of the shank relative to the handle.

Embodiment C.4.1 The device of embodiment C.4 in which the motor is capable of operating at two or more different speeds.

Embodiment C.5 The device of embodiment C further comprising a power source.

Embodiment B. A device comprising:
  a handle having a first end and a second end;
  a shank extending from the first end of the handle and terminating in a head;
  a motor operable to drive rotation of the shank relative to the handle, in which the motor is capable of operating at two or more different speeds/torques;
  a torque sensor;
  a twist sensor;
  an output device;
  a processor, in which the processor executes instructions to:
    receive an indication of a first torque reading taken by the torque sensor at a first time;
    receive an indication of a first twist reading taken by the twist sensor at the first time;
    receive an indication of a second torque reading taken by the torque sensor at a second time;
    receive an indication of a second twist reading taken by the twist sensor at the second time;
    determine a first slope of torque with respect to twist based on the indications of the first and second torque readings and based on the indications of the first and second twist readings;
    determine that the first slope does not fall with a predetermined range of values; and
    cause the output device to output an indication that the first slope does not fall with a predetermined range of values.

Embodiment B.1 The device of embodiment B in which the predetermined range of values includes a first value, a second value that is higher than the first value, a third range of values that includes values within a first percentage of the first value, and a fourth range of values that includes values within a second percentage of the second value.

Embodiment A. A device comprising:
  a handle having a first end and a second end;
  a shank extending from the first end of the handle and terminating in a head;
  a sensor;
  an output device;
  a processor, in which the processor executes instructions to:
    determine a parameter associated with a tissue;
    receive an indication of a first reading taken by the sensor at a first time;
    determine, based on the parameter and based on the indication of the first reading, a first speed;
    receive an indication of a second reading taken by the sensor at a second time;
    determine, based on the parameter and based on the indication of the second reading, a second speed; and
    cause the motor to operate at the second speed, in which the second speed does not equal the first speed.

Embodiment A.1 The device of embodiment A in which the sensor is a position sensor.

Embodiment A.2 The device of embodiment A in which the sensor is a torque sensor.

Embodiment A.3 The device of embodiment A in which the output device is a display screen.

Embodiment A.4 The device of embodiment A in which the output device is an audio speaker.

Embodiment A.5 The device of embodiment A further comprising a power source.

Embodiment A.6 The device of embodiment A in which the processor further executes instructions to cause the output device to output an indication of the first speed/torque.

CONSTRUCTION AND ARRANGEMENT

It is also important to note that the construction and arrangement of the elements of the driver 101 as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, algorithms, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

It is also to be understood that variations and modifications can be made on the aforementioned structures and methods without departing from the concepts of the present device, and further it is to be understood that such concepts are intended to be covered by the following claims unless these claims by their language expressly state otherwise.

It will be appreciated that any titles, headings, section headings, and the like used herein may be used for convenience or reference, but are not intended to be restrictive or limiting in any way. Descriptions appearing under or following a given heading are not intended to be limited in scope or in any other way by the heading.

It will be appreciated that various embodiments described herein are not limited in scope to the description appearing under the SUMMARY section, nor to the description appearing under the ABSTRACT section, nor to the description appearing in any other particular section. It will be appreciated that various embodiments described herein are not limited in scope to the description appearing under the FIELD section.

Applicants claim:

1. A device for driving a fastener into tissue, the device comprising:
   a handle having a first end and a second end;
   a shank extending from the first end of the handle and terminating in a head;
   one or more sensors;
   an output device; and
   a processor, in which the processor executes instructions to:
      receive a first set of readings from the one or more sensors during a first interval when the fastener is receding from the tissue;
      cause the output device to output a first signal indicative of the first set of readings;
      determine based on the first set of readings that the fastener has not previously advanced to a point of causing unintended damage;
      cause the output device to output a second signal based on the determination that the fastener has not previously advanced to a point of causing unintended damage to the tissue; and
      receive a second set of readings from the one or more sensors during a second interval when the fastener is advancing into the tissue,
      in which, in determining that the fastener has not previously advanced to a point of causing unintended damage, the processor executes instructions to compare the first set of readings to the second set of readings.

2. The device of claim 1 in which, in determining that the fastener has not previously advanced to a point of causing unintended damage, the processor executes instructions to:
   compare the first set of readings to the second set of readings; and
   determine that the first set of readings is similar to the second set of readings.

3. The device of claim 2 in which the first set of readings are representative of a first amount of friction encountered when the fastener is receding from the tissue, and the second set of readings are representative of second amount of friction encountered when the fastener is advancing into the tissue.

4. The device of claim 2 in which the first set of readings are representative of a first amount of torque encountered when the fastener is receding from the tissue, and the second set of readings are representative of second amount of torque encountered when the fastener is advancing into the tissue.

5. The device of claim 1 in which the processor further executes instructions to:
   determine, based on the first set of readings and based on the second set of readings, a first predicted maximum torque level that may be applied to the tissue without exceeding a predetermined level of risk of damaging the tissue;
   cause the output device to output a second signal indicative of the first predicted maximum torque level;
   determine a third set of readings;
   determine a second predicted maximum torque level that may be applied to the tissue without exceeding the predetermined level of risk of damaging the tissue, wherein the second predicted maximum torque level is determined as a non-zero adjustment to the first predicted maximum torque level based on the third set of readings; and
   cause the output device to output a third signal indicative of the second predicted maximum torque level.

6. The device of claim 1 in which the first set of readings and the second set of readings are obtained when the fastener is at the same number of turns into the tissue.

7. A device for driving a fastener into tissue, the device comprising:
   a handle having a first end and a second end;
   a shank extending from the first end of the handle and terminating in a head;
   one or more sensors;
   an output device; and
   a processor, in which the processor executes instructions to:
      receive a first set of readings from the one or more sensors during a first interval when the fastener is receding from the tissue;
      cause the output device to output a first signal indicative of the first set of readings;
      determine a first value of a material property of the tissue based on the first set of readings, wherein the material property is one of modulus, strength, and density;
      determine a second value of the material property of the tissue based on a second set of readings;
      compare the first value to the second value;
      determine that the second value is similar to the first value, thereby determining that the fastener has not previously advanced to a point of causing unintended damage; and
      cause the output device to output a second signal based on the determination that the fastener has not previously advanced to a point of causing unintended damage to the tissue.

* * * * *